US008067401B2

(12) United States Patent
Chepkwony et al.

(10) Patent No.: US 8,067,401 B2
(45) Date of Patent: *Nov. 29, 2011

(54) COMPOUNDS AND COMPOSITIONS FOR TREATING INFECTION

(75) Inventors: Paul Kiprono Chepkwony, Eldoret (KE); Maria Medina, Nairobi (KE); Mitchell Medina, Nairobi (KE)

(73) Assignee: International Patent Holdings LLC (KN)

( * ) Notice: Subject to any disclaimer, the term of this patent is extended or adjusted under 35 U.S.C. 154(b) by 661 days.

This patent is subject to a terminal disclaimer.

(21) Appl. No.: 11/899,914

(22) Filed: Sep. 6, 2007

(65) Prior Publication Data

US 2009/0069277 A1 Mar. 12, 2009

(51) Int. Cl.
| | |
|---|---|
| *A61K 31/58* | (2006.01) |
| *A61K 31/40* | (2006.01) |
| *A61K 31/4353* | (2006.01) |
| *A61K 31/352* | (2006.01) |
| *A61K 31/5025* | (2006.01) |
| *A61K 31/47* | (2006.01) |
| *A61K 31/44* | (2006.01) |
| *A61K 31/55* | (2006.01) |
| *A61P 29/00* | (2006.01) |

(52) U.S. Cl. ........ 514/176; 514/419; 514/280; 514/307; 514/299; 514/292; 514/414; 514/215; 514/314; 514/285; 514/453; 514/257

(58) Field of Classification Search .................. 514/176
See application file for complete search history.

(56) References Cited

U.S. PATENT DOCUMENTS

| | | | |
|---|---|---|---|
| 5,178,865 A | 1/1993 | Ho et al. | |
| 5,366,725 A | 11/1994 | Okubo et al. | |
| 5,411,733 A | 5/1995 | Hozumi et al. | |
| 5,837,257 A | 11/1998 | Tsai et al. | |
| 5,989,556 A | 11/1999 | Tsai et al. | |
| 6,455,078 B1 | 9/2002 | Wu | |
| 6,696,094 B2 | 2/2004 | Wu | |
| 7,329,767 B2 * | 2/2008 | Dewis et al. | .................. 554/35 |
| 7,674,483 B2 | 3/2010 | Chepkwony | |
| 2010/0189828 A1 | 7/2010 | Chepkwony | |

FOREIGN PATENT DOCUMENTS

| | | |
|---|---|---|
| EP | 1919490 | 3/2007 |
| WO | WO 2007/024510 | 3/2007 |

OTHER PUBLICATIONS

Marion (The Alkaloids of the Indole Series, Council National of Researches of Ottawa, 1941, pp. 305-308, translated from French).*
Edeoga (phytochemical constituents of some Nigerian medicinal plants, African Journal of Biotechnology vol. 4 (7) pp. 685-699, 2005).*
U.S. Appl. No. 11/352,931, filed Feb. 13, 2006.

International search report issued Dec. 27, 2007 in connection with PCT Application No. pct/us2006/031355.
Written opinion of the international search authority issued Feb. 22, 2008 in connection with pct Application No. pct/us2006/031355.
International preliminary report on Patentability, issued Feb. 26, 2008 in connection with pct Application No. pct/us2006/031355.
Extended European search reporting issued Apr. 8, 2010 in connection with European Patent Application No. 06801240.0.
In Response to the Communication Dated Apr. 8, 2010 in connection with European Patent Application No. 06801240.0.
Notice of Allowance issued Aug. 18, 2011 in connection with U.S. Appl. No. 12/657,212, filed Jan. 15, 2010.
Response to Apr. 1, 2011 Office Action in connection with U.S. Appl. No. 12/657,212, filed Jan. 15, 2010.
Office Action issued Apr. 1, 2011 in connection with U.S. Appl. No. 12/657,212, filed Jan. 15, 2010.
Response to Oct. 13, 2010 Office Action in connection with U.S. Appl. No. 12/657,212, filed Jan. 15, 2010.
Office Action issued Oct. 13, 2010 in connection with U.S. Appl. No. 12/657,212, filed Jan. 15, 2010.
Notice of Allowance issued Oct. 19, 2009 in connection with U.S. Appl. No. 12/387,896, filed May 8, 2009.
Notice of Allowance issued Apr. 7, 2009 in connection with U.S. Appl. No. 11/352,931, filed Feb. 13, 2006.
Examiner Interview Summary Record issued Apr. 7, 2009 in connection with U.S. Appl. No. 11/352,931, filed Feb. 13, 2006.
Final Office Action issued Apr. 7, 2009 in connection with U.S. Appl. No. 11/352,931, filed Feb. 13, 2006.
Response to Feb. 8, 2008 Office Action in connection with U.S. Appl. No. 11/352,931, filed Feb. 13, 2006.
Office Action issued Feb. 8, 2008 in connection with U.S. Appl. No. 11/352,931, filed Feb. 13, 2006.
Response to Jul. 20, 2007 Office Action in connection with U.S. Appl. No. 11/352,931, filed Feb. 13, 2006.
Office Action issued Jul. 20, 2007 in connection with U.S. Appl. No. 11/352,931, filed Feb. 13, 2006.
Communication pursuant to rule 94(3) epc issued Oct. 15, 2010 in connection with European Patent Application No. 06801240.0.
In Response to the Communication Dated Oct. 15, 2010 in connection with European Patent Application No. 06801240.0.
Communication pursuant to rule 94(3) epc issued Sep. 12, 2011 in connection with European Patent Application No. 06801240.0; (Exhibit 23).
Asres et al., Antiviral Activity Against Human Immunodeficiency Virus Type 1 (HIV-1) and Type 2 (HIV-2) of . . . Plants, Phytother, Res. 15, 62-69 (2001).
Baldascini, "Income generating opportunities arising from natural exosystems in Uganda; an overview." The International Food Policy institute. 2002, p. 1-39.
Broutin et al. "Whooping Cough metapopulation Dynamics in tropical conditions: persistence impact of vaccination" Proc. R. Soc. Lond. B(suppl). 271. 2004. p. S302-S305.
Chang, et al., "Differential inhibition of reverse transcriptase and cellular DNA polymerase-α activities by lignans isolated . . . " Antiviral Research, 27(4), 367-374 (1995).
Cos, et al., "Antiviral activity of Rwandan medicinal plants against human immunodeficiency virus type-1 (HIV-1)", Phytomedicine, 9, 62-68 (2002).

(Continued)

*Primary Examiner* — Kathrien Cruz
(74) *Attorney, Agent, or Firm* — Cooper & Dunham LLP

(57) ABSTRACT

Compounds from 14 Kenyan plants, including from the root of *Dovyalis abyssinica* and *Clutia robusta* have been characterized and isolated, and their uses are disclosed.

13 Claims, 1 Drawing Sheet

OTHER PUBLICATIONS

Cos et al. "Further evaluation of Rwandan medicinal plant extracts for their antimicrobial and antiviral activities," J Ethnopharmacol (2002) 79:155-163. Abstract only.

Cui et al., "Clinical efficacy of compound periploca liquid in treating condyloma acuminaturn and . . . " Zhongguo Zhong Xi Yi Jie He Za Zhi (2005) 25:392-6. Abstract only.

DeBoer et al., "Anti-fungal and anti-bacterial activity of some herbal . . ." J Ethnopharmacol (2005) Available online Nov. 11, 2004, vol. 96, p. 461-469. Abstract only.

Eloff, "Which extractant should be used for the screening and isolation of antimicrobial components from plants?" Journal of Ethnopharmacology (1998) 60:1-8. Abstract only.

Geyid et al, "Screening of some medicinal plants of Ethiopia for their anti-microbial properties and chemical profiles", J. Ethnopharmacology (2005) 97:421-427, Abstract only.

Giday, "An ethnobotanical study of medicinal plants used by the Zay people in Ethiopia" , CBMs: s Skriftseria (2001) 1:81-99.

Houghton, et al., "A Clinical Evaluation of the Chinese Herbal Mixture 'Aden-I' for Treating Respiratory Infections", Phytother. Res., 7(5), 384-386 (1993).

John, et al., "Synergistic Antiretroviral Activities of the Herb, *Prunella vulgaris*, with AZT, ddl, and ddc", Abstr. Gen. Meet., Am. Sc. Microbiol., 94, 481 (1994).

Kane, et al., Methyl Gallate, "Methyl-3, 4, 5-trihydroxy-benzoate, is a Potent and Highly Specific Inhibitor of Herpes . . . " Bioscience Report, 8, 85-94 (1988).

Kuritzkes, "Laboratory Tests for Monitoring HIV-1 infection", HIV and Hepatitis,com, p. 1-24 (2001).

Kraft et ale , In vitro antiplasmodial evaluation of medicinal plants from Zimbabwe Phytotherapy Research (2003) 17:123-128. Abstract only.

Mulholland et ale , "The Chemistry of the Meliaceae and Ptaeroxylaceae of Southern and Eastern Africa and Madagascar" Current Organic Chemistry (2002) 4:1011-1054.

Nagai, et al., "Inhibition of influenza Virus Sialidas and Anti-influenza Virus Activity by Plant Flavonoids", Chem. Pharm Bull. 38(5), 1329-1332 (1990).

Tabbe, et al., "Isolation, purification, and partial characterization of pruneilin, an anti-HIV component from . . . ", Antiviral Research, , 263-273 (1989).

Takechi and Tanaka, "Purification and Characterization of Antiviral Substance from the Bud of *Syzygium aromatica*", Planta Medica, 42, 69-74 (1981).

Vecchiato, "Sociocultural Aspects of Tuberculosis Control in Ethiopis", Medical Anthropology Quarterly, 11(2):183-201 (1997).

Verschaeve et al, "Investigation of the antimutagenic effects of selected South African medicinal plant extracts", Toxicology in Vitro (2004) 18:29-35. Abstract only.

Wikipedia.org. Retrieved from the internet. <http://en.wikipedia.org/wiki/infectious_disease> Retrieved on Mar. 25, 2011. pp. 1-12.

Yamasaki, et al., "Screening Test of Crude Drug Extract on Anti-HIV Activity", Yakugaku Zasshi, 113(11), 818-824 (1993).

Yao, et al., "Mechanism of Inhibition of HIV-1 Infection in Vitro by Purified Extract of *Prunella vulgaris*", Virology, 187(1), 56-62 (1992).

Yamada, "A Report on the Ethnobotany of the Nyindu in the Eastern Part of the Former Zaire" , African Study Monographs (1999) 20:1-72.

* cited by examiner

COMPOUNDS AND COMPOSITIONS FOR TREATING INFECTION

BACKGROUND OF THE INVENTION

Tens of millions of people world-wide are living with acquired immunodeficiency syndrome (AIDS), or are infected with the causative agent, human immunodeficiency virus (HIV). In some countries in sub-Saharan Africa, up to one in four adults has contracted the disease. Despite the costs and efforts spent attempting to identify new methods of treatment, a cure for the disease has remained elusive.

Ancient societies have traditionally turned to plants for their health needs. Documented use of herbs to treat illnesses dates back to as early as 2,000 B.C. Recently, individuals have resorted to nature as remedies and medicines for the treatment of modern illnesses have been derived from plants, such as for example, treatment of HIV and other infectious diseases.

For example, U.S. Pat. No. 5,178,865 discloses an experimental treatment with 56 herbs, and reports that 10 of the 56 herbs exhibit anti-HIV activity in in vitro experiments. The 10 herbs include: *Coptis chineusis, Ligusticum wallichii, Ilicium eanclolatum, Isatis tinctoria, Salvia miltiorrhiza, Erycibe obtusifolia, Acanthopanax graciliatylus, Bostaurus domesticus, Inula helenium* and *Lonicera japonica*. Both *Bostaurus domesticus* and *Lonicera japonica* are further described to be able to combine with *Scutellaria baicaleusis* to exhibit anti-HIV activity.

U.S. Pat. No. 5,837,257 discloses Chinese herbal medicines that exhibit in vitro antiviral activity against murine leukemia virus and HIV and for treatment of animals and humans infected with HIV. In one of the preferred embodiments, the Chinese herbal medicines contain *hedyotis, Scutellarial barbatae herba, Lonicera flos, Prunellae spica* and *Solani harba*.

U.S. Pat. No. 5,989,556 discloses various herbal compositions for treating viral infections which have shown in vitro antiviral activities against HIV. A first herbal composition contains *Aeginetiae herba, Blechni rhizoma, Lespedezae herba, Polygoni cuspidati rhizoma, Forsythiae fructus,* and *Ligustri fructus*. A second herbal composition contains *Cirsii rhizoma* and *radix, Breeae radix, Baphicacanthis rhizoma* and *radix, Phellodendri cortex,* and *Bletillae tuber*. A third herbal composition disclosed in the patent includes *Aeginetiae Herba, Lonicerae, Flos, Prunellae spica* and *Lespedezal herba*.

U.S. Pat. No. 6,696,094 discloses an herbal pharmaceutical composition for treating HIV/AIDS. The pharmaceutical composition contains 14 ingredients, including: diffuse *hedyotis*, bistort rhizome, giant knotweed rhizome, Asiatic moonseed rhizome, baical skullcap root, Bovine biliary powder, milkvetch root, barbary wolfberry fruit, sanqi, figwort root, Chinese magnoliavine fruit, turmeric root-tuber, hawthorn fruit and Chinese *angelica*. Procedures are provided for the preparation of an "HIVCIDE condensate", which can be formulated as an injectable solution or as capsules. Results indicate that subjects injected with HIVCIDE solution showed no symptoms of acute or chronic toxicity. Further, the HIVCIDE injection solution was effective in inhibiting pathological changes in cells caused by HIV-1 in vitro. In a third experiment, the HIVCIDE injection solution was effective in reducing symptoms of HIV-infected subjects in a treatment regime together with administration of HIVCIDE capsules. HIV-positive subjects did not show adverse reactions to HIVCIDE injection solution. It was further reported three out of four subjects showed improvement in fatigue after treatment with HIVCIDE, and that HIV viral load studies indicated that all subjects demonstrated reduced HIV viral loads.

U.S. Pat. No. 6,455,078 discloses a medical herbal composition for treating liver diseases and HIV. The composition contains 15 ingredients, which includes diffuse *hedyotis*, bistort rhizome giant knotweed rhizome, Asiatic moonseed rhizome, baical skullcap root, bovine biliary powder, milkvetch root, barbary wolfberry fruit, sanqi, red gingseng, figwort root, Chinese magnoliavine fruit, turmeric root-tuber, hawthorn fruit and Chinese *angelica*. Among the 15 ingredients, diffuse *hedyotis*, bistort rhizome, giant knotweed rhizome, and Chinese magnoliavine fruit are cited as being necessary to contribute to the efficacy of the pharmaceutical composition.

In U.S. Pat. No. 5,366,725, an extract from the seeds of *Aeginetia indica* was prepared which exhibited excellent carcinostatic effects and possesses interleukin-2 and interferon-gamma-inducing properties. The extract is believed to be a macromolecular polysaccharide, which may or may not contain Lipid A binding with protein depending on whether the extraction is conducted using butanol or phenol. The extracted substance is soluble in water, insoluble in n-butanol, and has a molecular weight ranging from 100,000 to 200,000 Daltons.

U.S. Pat. No. 5,411,733 to Hozumi, et al., discloses a variety of plant extracts for use as anti-herpes viral, anti-polioviral, anti-varicella-zoster virus, anti-measles virus, anti-cytomegalovirus (CMV), and anti-DNA and anti-RNA virus agents.

U.S. Pat. No. 5,178,865 discloses the anti-HIV activity in vitro of a variety of herbs known in China to exhibit anti-viral activity. Water extractions of the mixtures, treatment with ethanol for precipitation and charcoal adsorption are disclosed for the preparation for the anti-HIV-active composition.

Two lignans, phyllamycin B and retrojusticiden B, have been reported to have an inhibitory effect on HIV-1 reverse transcriptase activity. The lignans are isolated from *Phyllanthus myrtifolius Moon*, a plant widely grown in Southern China. See, for example, Chang, et al., Antiviral Research, 27 (4), 367-374 (1995).

A mixture of aqueous extracts of *Lonicera japonica* flower buds, *Forsythia suspensa* fruits, and *Scutellaria baicalensis* rootbark have been shown to have antibacterial and antiviral properties. Subjects with severe respiratory disease treated with the mixture responded as well as a control group on standard antibiotic therapy. See Houghton, et al., *Phytother. Res.* 7(5), 384-386 (1993).

A water extract of *Prunella vulgaris* was reported to have anti-HIVB activity when administered in combination with zidovudine (AZT) and didanosine (dd1). Only a slight additive effect was observed for the administration of an extract of *Prunella vulgaris* and *zalcitabine* (ddC). See John, et al., *Abstr. Gen. Meet. Am. Sc. Microbiol*, 94, 481 (1994).

Yamasaki et al. have reported the in vitro evaluation of 204 crude drugs commonly used in Japan for anti-HIV-1 activity and studies indicate that hot water extracts of *Lithospermum erythrorhizon* (root) and *Prunella vulgaris* (spike) showed strong in vitro anti HIV-1 activity with an $IC_{100}$ of 16 .mu.g/mL. See Yamasaki, et al., *Yakugaku Zasshi* 113(11), 818-824 (1993).

Yao et al. have reported that water extracts of dried *Prunella vulgaris* (whole plant) were active in vitro for inhibiting HIV-1 replication, and showed relatively low cytotoxicity to MT-4 cells. The extract also demonstrated activity in the inhibition of reverse transcriptase. The active factor was purified and identified as anionic with a molecular weight of approximately 10,000 Daltons. This active component may be the same as the prunellin, as described by Tabba. See Tabba, et al., *Antiviral Research* 11, 263-273 (1989). The purified extract inhibited HIV-1 replication in the lymphoid cell line MT-4, in the monocytoid cell line U937, and in peripheral blood mononuclear cells (PBMC) at effective concentrations of 6.3 and 12.5 .mu.g/mL, respectively. Pretreatment of uninfected cells with the extract prior to viral exposure did not prevent HIV-1 infection upon subsequent exposure to the virus. Preincubation with the purified extract decreased HIV-1 infectiousness. The purified extract also blocked cell-to-cell transmission of HIV-1, prevented syncytium formation, and interfered with the ability of both HIV-1 and purified gp 120 to bind to CD4. PCR (polymerase chain reaction) analysis confirmed the absence of HIV-1 proviral DNA in cells exposed to virus in the presence of the extract, suggesting that the purified extract antagonized HIV-1 infection of susceptible cells by preventing viral attachment to the CD4 receptor. See Yao, et al., *Virology* 187(1), 56-62 (1992).

Tabba, et al. isolated and partially characterized prunellin, a compound exhibiting anti-HIV properties, from aqueous extracts of *Prunella vulgaris*, a Chinese herb. Prunellin was identified as a carbohydrate (a partially sulfated polysaccharide) with an minimum inhibition concentration of 2.2 µg/mL against HIV-1 in vitro. It was identified as having a molecular weight of about 10,000 Dalton. See Tabba, et al., *Antiviral Research* 11, 263-273 (1989).

Antiviral agents have been isolated from *Syzygium aromatica, Sapium sebiferum* (Chinese tallow tree leaves), *Scutellaria baicalensis,* and *Scutellaria rivularis*. Eugeniin, (a tannin isolated from *Syzygium aromatics*), and methyl gallate, (isolated from *Sapium sebiferum*), exhibited anti-herpes simplex virus (HSV-2) activity in vitro. Plant flavonoids, such as 5,7,4-truhydroxyflavone, extracted from the whole herb *Scutellaria rivularis*, were reported to have anti-influenza virus activity. See Hozumi, et al., U.S. Pat. No. 5,411,733; Takechi, et al., *Planta Medica* 42, 69-74 (1981); Kane, et al., *Bioscience Report* 8, 85-94 (1988); and Nagai, et al., *Chem. Pharm Bull.* 38(5), 1329-1332 (1990).

Ethiopian medicinal plants known for treatment of a variety of ailments were screened for activity against HIV-1 and HIV-2, as reported by Asres, et al. Extracts from *Bersama abyssinica* root bark, *Combretum paniculatum* leaves, *Dodonaea angustfolia* leaves, and *Ximenia Americana* stem bark each displayed anti-viral activity at concentrations that were non-toxic to MT-4 cells. Anti-viral activity of the extracts is noted to be more effective against HIV-1 than HIV-2. See Asres, et al., *Phytother. Res.*, 15, 62-69 (2001).

Selected plants used in traditional Rwandan medicine for treatment of infections and/or rheumatoid diseases were investigated for antiviral activity in vitro against HIV-1. See Cos, et al., *Phytomedicine* 9, 62-68 (2002). Of 38 plant extracts tested, extracts from the leaves of *Aspilia pluriseta* and *Rumex bequaertii* had the highest antiviral activities.

SUMMARY

Disclosed is a composition comprising:
(a) at least one of the following isolated compounds: N-Methyl-L-tryptophan; 1,2-Methylenedioxy-9-hydroxy-10-methoxynoraporphine; 6-(1,2,3,4-Tetrahydro-6,7-dimethoxy-2-methyl-1-isoquinolinyl)furo[3,4-e]-1,3-benzodioxol-8(6H)-one; or [1,α,3β(E),5α,6α,7α]-2-Methyl-2-butenoic acid-6,7-dihydroxy-8-methyl-8-azabicyclo[3.2.1]oct-3-yl ester, and (b) at least one of the following isolated compounds: (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline; 3β-(Hydroxymethyl)-2α-methyl-4β-[(9-methyl-9H-pyrido[3,4-b]indol-1-yl)methyl]-2H-pyran-5-carboxylic acid methyl ester; or (3aS-cis)-1,2,3,3a,8,8a-Hexahydro-1,3a,8-trimethylpyrrolo[2,3-b]indol-5-ol methylcarbamate(ester). The composition may have a carrier.

Also disclosed is a composition consisting essentially of a carrier and at least two alkaloid compounds, wherein the at least two alkaloid compounds are:
(a) N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one; or
[1,α,3β(E),5α,6α,7α]-2-Methyl-2-butenoic acid-6,7-dihydroxy-8-methyl-8-azabicyclo[3.2.1]oct-3-yl ester, and
(b) (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; or
(3aS-cis)-1,2,3,3a,8,8a-Hexahydro-1,3a,8-trimethylpyrrolo[2,3-b]indol-5-ol methylcarbamate (ester).

DETAILED DESCRIPTION OF THE INVENTION

Figure 1:
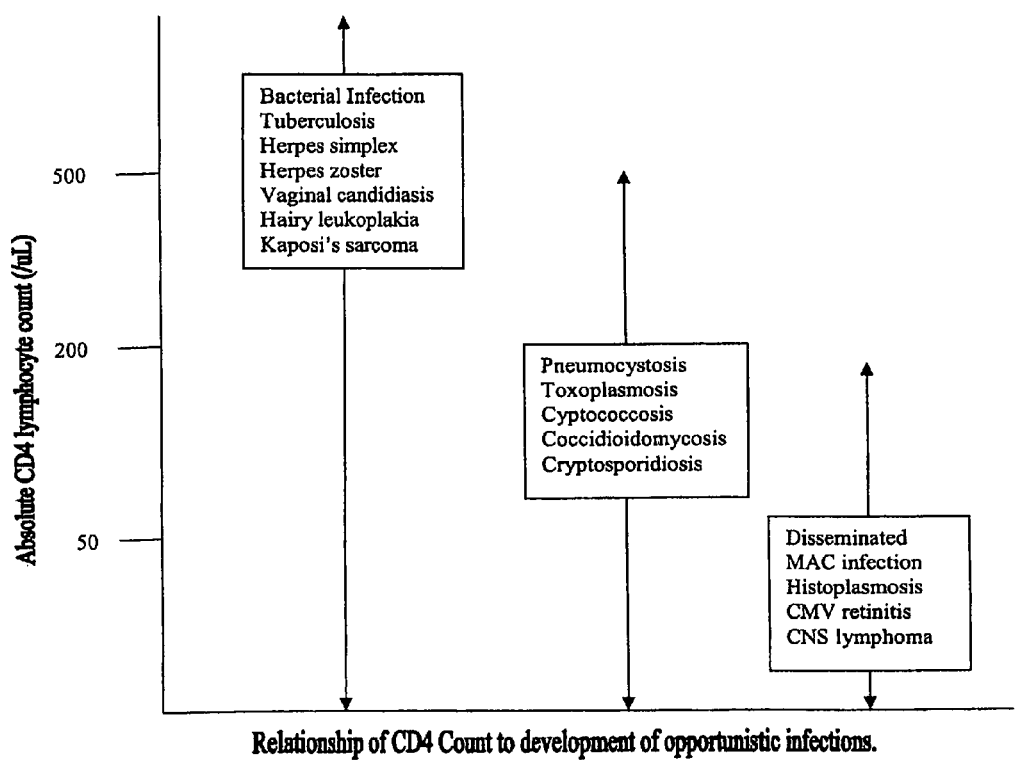
FIG. 1
This Figure shows relationships between observed clinical symptomatology and CD4+ count results.

Disclosed is a composition comprising:
(a) at least one of the following isolated compounds: N-Methyl-L-tryptophan; 1,2-Methylenedioxy-9-hydroxy-10-methoxynoraporphine; 6-(1,2,3,4-Tetrahydro-6,7-dimethoxy-2-methyl-1-isoquinolinyl)furo[3,4-e]-1,3-benzodioxol-8(6H)-one; or [1,α,3β(E),5α,6α,7α]-2-Methyl-2-butenoic acid-6,7-dihydroxy-8-methyl-8-azabicyclo[3.2.1]oct-3-yl ester,
(b) at least one of the following isolated compounds: (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline; 3β-(Hydroxymethyl)-2α-methyl-4β-[(9-methyl-9H-pyrido[3,4-b]indol-1-yl)methyl]-2H-pyran-5-carboxylic acid methyl ester; or (3aS-cis)-1,2,3,3a,8,8a-Hexahydro-1,3a,8-trimethylpyrrolo[2,3-b]indol-5-ol methylcarbamate(ester), and (c) a carrier.

In an embodiment, the composition may comprise the following isolated compounds:
N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one;
[1,α,3β(E),5α,6α,7α]-2-Methyl-2-butenoic acid-6,7-dihydroxy-8-methyl-8-azabicyclo[3.2.1]oct-3-yl ester;
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;

3β-(Hydroxymethyl)-2α-methyl-4β-[(9-methyl-9H-pyrido[3,4-b]indol-1-yl)methyl]-2H-pyran-5-carboxylic acid methyl ester;

(3aS-cis)-1,2,3,3a,8,8a-Hexahydro-1,3a,8-trimethylpyrrolo[2,3-b]indol-5-ol methylcarbamate(ester); and a carrier.

In a further embodiment, the composition may further comprise at least one of the following isolated compounds:

(1α,2β)-3,12-Dihehydro-9,10-[methylenebis(oxy)]galanthan-1,2-diol;

(3β,12α)-Solanid-5-ene-3,12-diol;

1-(6-methoxy-4-quinolyl)-3-(3-vinyl-4-piperidyl)-1-propanone;

(E,E,Z)-N-isobutyl-2,6,8-decatrienamide; 2,3,5,6-tetramethoxyphenanthro[9,10:6',7']indolizidine;

5,7,8,15-Tetrahydro-3,4-dimethoxy-6-methylbenzo[e][1,3]dioxolo[4,5-k][3]benzazecin-14(6H)-one;

(1S,6S,7R,8R,8aR)-Octahydro-indolizinetetrol;

(3S,4R)-Dihydro-3-[(R)-hydroxyphenylmethyl]-4-[(1-methyl-1H-imidazol-5-yl)methyl]-2(3H)-furanone;

(3S-cis)-3-Ethyldihdroxy-4-[(-methyl-1H-imidazol-5-yl)methyl]-2(3H)-furanone;

(S)-4-Ethyl-4-hydroxy-1H-pyrano[3'4':6,7]indolizino[1,2-b]quinoline-3,14(4H,12H)-dione;

1,2,3,4-Tetrahydro-6,7-dimethoxy-8-isoquinolinol;

1,2,3,4-Tetrahydro-6,7-dimethoxy-1-methyl-8-isoquinolinol;

N-(7S)-5,6,7,9-Tetrahydro-1,2,3,10-tetramethoxy-9-oxobenzo[a]heptalen-7-yl)acetamide;

1αH,5αH-tropan-3α-ol atropate;

1,2-(methylenedioxy)-6aβ-aporphin-11-ol;

(16α,17α)-17-Hydroxyyohimban-16-carboxylic acid methyl ester;

trans-8-methyl-N-vanillyl-6-nonenamide;

1,2-(methylenedioxy)aporphine;

(1R-trans)-2,3,5,7a-Tetrahydro-1-hydroxy-1H-pyrrolizine-7-methanol;

[1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;

(3α,14β,16α)-14,15-Dihydro-14-hydroxyeburnamenine-14-carboxylic acid methyl ester;

1,10-Dimethoxy-6aα-aporhine-2,9-diol;

6,7,12b,13-Tetrahydro-4H-bis[1,3]benzodioxolo[5,6-a:4',5'-g]quinolizine;

(8β)-8-methoxy-16-methyl-2,3:10,11-bis[methylenebis(oxy)]rheadan;

6',7',10,11-Tetramethoxyemetan;

3-(-Benzoyloxy)-8-methyl-8-azabicyclo[3.2.1]octane-2-carboxylic acid;

8,13,13b,14-Tetrahydro-14-methylindolo[2',3':3,4]pyrido[2,1-b]quinazolin-5(7H)-one;

6',12'-Dimethoxy-2,2'-dimethyl-6,7-[methylenebis(oxy)]oxyacanthan;

4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;

5,11-Dimethyl-6H-pyrido[4,-3b]carbazole;

6,7-Dihydro-1,2,3,10-tetramethoxy-7-(methylamino)benzo[a]heptalen-9(5H)-one;

(1α)-2,3-Didehydro-7-methoxycrinan-1-ol; or (1α,3α)-7-methoxycrinan-1,3-diol.

In yet a further embodiment, the composition may comprise the following isolated compounds:

N-Methyl-L-tryptophan;

1,2-Methylenedioxy-9-hydroxy-10-methoxynoraporphine;

6-(1,2,3,4-Tetrahydro-6,7-dimethoxy-2-methyl-1-isoquinolinyl)furo[3,4-e]-1,3-benzodioxol-8(6H)-one;

[1,α,3β(E),5α,6α,7α]-2-Methyl-2-butenoic acid-6,7-dihydroxy-8-methyl-8-azabicyclo[3.2.1]oct-3-yl ester;

(6aS)-9-[4,5-Dimethoxy-2-[[(1S)-1,2,3,4-tetrahydro-6,7-dimethoxy-2-methyl-1-isoquinolinyl]methyl]phenoxyl]-5,6,6a,7-tetrahydro-1,2,10-trimethoxy-6-methyl-4H-dibenzo[de, g]quinoline;

3β-(Hydroxymethyl)-2α-methyl-4β-[(9-methyl-9H-pyrido[3,4-b]indol-1-yl)methyl]-2H-pyran-5-carboxylic acid methyl ester;

(3aS-cis)-1,2,3,3a,8,8a-Hexahydro-1,3a,8-trimethylpyrrolo[2,3-b]indol-5-ol methylcarbamate(ester);

(1α,2β)-3,12-Dihehydro-9,10-[methylenebis(oxy)]galanthan-1,2-diol;

(3β,12α)-Solanid-5-ene-3,12-diol;

1-(6-methoxy-4-quinolyl)-3-(3-vinyl-4-piperidyl)-1-propanone;

(E,E,Z)-N-isobutyl-2,6,8-decatrienamide;

2,3,5,6-tetramethoxyphenanthro[9,10:6',7']indolizidine;

5,7,8,15-Tetrahydro-3,4-dimethoxy-6-methylbenzo[e][1,3]dioxolo-[4,5-k][3]benzazecin-14(6H)-one;

(1S,6S,7R,8R,8aR)-Octahydro-indolizinetetrol;

(3S,4R)-Dihydro-3-[(R)-hydroxyphenylmethyl]-4-[(1-methyl-1H-imidazol-5-yl)methyl]-2(3H)-furanone;

(3S-cis)-3-Ethyldihdroxy-4-[(-methyl-1H-imidazol-5-yl)methyl]-2(3H)-furanone;

(S)-4-Ethyl-4-hydroxy-1H-pyrano[3'4':6,7]indolizino[1,2-b]quinoline-3,14(4H,12H)-dione;

1,2,3,4-Tetrahydro-6,7-dimethoxy-8-isoquinolinol;

1,2,3,4-Tetrahydro-6,7-dimethoxy-1-methyl-8-isoquinolinol;

N-(7S)-5,6,7,9-Tetrahydro-1,2,3,10-tetramethoxy-9-oxobenzo[a]heptalen-7-yl)acetamide;

1αH,5αH-tropan-3α-ol atropate;

1,2-(methylenedioxy)-6aβ-aporphin-11-ol;

(16α,17α)-17-Hydroxyyohimban-16-carboxylic acid methyl ester;

trans-8-methyl-N-vanillyl-6-nonenamide;

1,2-(methylenedioxy)aporphine;

(1R-trans)-2,3,5,7a-Tetrahydro-1-hydroxy-1H-pyrrolizine-7-methanol;

[1R-(1α,2E,4aα,4bβ,8aα,10aβ)]-(Dodecahydro-7-hydroxy-1,4b,8,8-tetramethyl-10-oxo-2(H)-phenanthrenylidene)acetic acid 2-(dimethylamino)ethyl ester;

(3α,14β,16α)-14,15-Dihydro-14-hydroxyeburnamenine-14-carboxylic acid methyl ester;

1,10-Dimethoxy-6aα-aporhine-2,9-diol;

6,7,12b,13-Tetrahydro-4H-bis[1,3]benzodioxolo[5,6-a:4',5'-g]quinolizine;

(8β)-8-methoxy-16-methyl-2,3:10,11-bis[methylenebis(oxy)]rheadan;

6',7',10,11-Tetramethoxyemetan;

3-(-Benzoyloxy)-8-methyl-8-azabicyclo[3.2.1]octane-2-carboxylic acid;

8,13,13b,14-Tetrahydro-14-methylindolo[2',3':3,4]pyrido[2,1-b]quinazolin-5(7H)-one;

6',12'-Dimethoxy-2,2'-dimethyl-6,7-[methylenebis(oxy)]oxyacanthan;

4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;

5,11-Dimethyl-6H-pyrido[4,-3b]carbazole;

6,7-Dihydro-1,2,3,10-tetramethoxy-7-(methylamino)
benzo[a]heptalen-9(5H)-one;
(1α)-2,3-Didehydro-7-methoxycrinan-1-ol; and
(1α,3α)-7-methoxycrinan-1,3-diol, and a carrier.

Also disclosed is a composition comprising (a) at least one of the following isolated compounds:

N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one; or
[1,α,3β(E),5α,6α,7α]-2-Methyl-2-butenoic acid-6,7-dihydroxy-8-methyl-8-azabicyclo[3.2.1]oct-3-yl ester,
and (b) at least one of the following isolated compounds:
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; or
(3aS-cis)-1,2,3,3a,8,8a-Hexahydro-1,3a,8-trimethylpyrrolo[2,3-b]indol-5-ol methylcarbamate(ester).

Also disclosed is a composition consisting essentially of a carrier and at least two alkaloid compounds, wherein the at least two alkaloid compounds are:

(a) N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one; or
[1,α,3β(E),5α,6α,7α]-2-Methyl-2-butenoic acid-6,7-dihydroxy-8-methyl-8-azabicyclo[3.2.1]oct-3-yl ester, and (b) (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; or
(3aS-cis)-1,2,3,3a,8,8a-Hexahydro-1,3a,8-trimethylpyrrolo[2,3-b]indol-5-ol methylcarbamate (ester).

In an embodiment, such a composition may consist essentially of a carrier and at least the following alkaloid compounds:
N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one;
[1,α,3β(E),5α,6α,7α]-2-Methyl-2-butenoic acid-6,7-dihydroxy-8-methyl-8-azabicyclo[3.2.1]oct-3-yl ester;
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; and
(3aS-cis)-1,2,3,3a,8,8a-Hexahydro-1,3a,8-trimethylpyrrolo[2,3-b]indol-5-ol methylcarbamate (ester).

In a further embodiment, the composition may further consist essentially of the following alkaloid compound:

(1α,2β)-3,12-Dihehydro-9,10-[methylenebis(oxy)]galanthan-1,2-diol;
(3β,12α)-Solanid-5-ene-3,12-diol;
1-(6-methoxy-4-quinolyl)-3-(3-vinyl-4-piperidyl)-1-propanone;
(E,E,Z)-N-isobutyl-2,6,8-decatrienamide; 2,3,5,6-tetramethoxyphenanthro[9,10:6',7']indolizidine;
5,7,8,15-Tetrahydro-3,4-dimethoxy-6-methylbenzo[e][1,3]dioxolo[4,5-k][3]benzazecin-14(6H)-one;
(1S,6S,7R,8R,8aR)-Octahydro-indolizinetetrol;
(3S,4R)-Dihydro-3-[(R)-hydroxyphenylmethyl]-4-[(1-methyl-1H-imidazol-5-yl)methyl]-2(3H)-furanone;
(3S-cis)-3-Ethyldihdroxy-4-[(-methyl-1H-imidazol-5-yl)methyl]-2(3H)-furanone;
(S)-4-Ethyl-4-hydroxy-1H-pyrano[3'4':6,7]indolizino[1,2-b]quinoline-3,14(4H,12H)-dione;
1,2,3,4-Tetrahydro-6,7-dimethoxy-8-isoquinolinol;
1,2,3,4-Tetrahydro-6,7-dimethoxy-1-methyl-8-isoquinolinol;
N-(7S)-5,6,7,9-Tetrahydro-1,2,3,10-tetramethoxy-9-oxobenzo[a]heptalen-7-yl]acetamide;
1αH,5αH-tropan-3α-ol atropate;
1,2-(methylenedioxy)-6aβ-aporphin-11-ol;
(16α,17α)-17-Hydroxyyohimban-16-carboxylic acid methyl ester;
trans-8-methyl-N-vanillyl-6-nonenamide;
1,2-(methylenedioxy)aporphine;
(1R-trans)-2,3,5,7a-Tetrahydro-1-hydroxy-1H-pyrrolizine-7-methanol;
[1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;
(3α,14β,16α)-14,15-Dihydro-14-hydroxyeburnamenine-14-carboxylic acid methyl ester;
1,10-Dimethoxy-6aα-aporhine-2,9-diol;
6,7,12b,13-Tetrahydro-4H-bis[1,3]benzodioxolo[5,6-a:4α,5α-g]quinolizine;
(8β)-8-methoxy-16-methyl-2,3:10,11-bis[methylenebis(oxy)]rheadan;
6',7',10,11-Tetramethoxyemetan;
3-(-Benzoyloxy)-8-methyl-8-azabicyclo[3.2.1]octane-2-carboxylic acid;
8,13,13b,14-Tetrahydro-14-methylindolo[2',3':3,4]pyrido[2,1-b]quinazolin-5(7H)-one;
6',12'-Dimethoxy-2,2'-dimethyl-6,7-[methylenebis(oxy)]oxyacanthan;
4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxy]phenol;
5,11-Dimethyl-6H-pyrido[4,-3b]carbazole;
6,7-Dihydro-1,2,3,10-tetramethoxy-7-(methylamino)benzo[a]heptalen-9(5H)-one;
(1α)-2,3-Didehydro-7-methoxycrinan-1-ol; or
(1α,3α)-)-7-methoxycrinan-1,3-diol.

Yet in a further embodiment the composition may consist essentially of a carrier and the following alkaloid compounds:
N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one;
[1,α,3β(E),5α,6α,7α]-2-Methyl-2-butenoic acid-6,7-dihydroxy-8-methyl-8-azabicyclo[3.2.1]oct-3-yl ester;
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester;
(3aS-cis)-1,2,3,3a,8,8a-Hexahydro-1,3a,8-trimethylpyrrolo[2,3-b]indol-5-ol methylcarbamate(ester);
(1α,2β)-3,12-Dihehydro-9,10-[methylenebis(oxy)]galanthan-1,2-diol;
(3β,12α)-Solanid-5-ene-3,12-diol;
1-(6-methoxy-4-quinolyl)-3-(3-vinyl-4-piperidyl)-1-propanone;
(E,E,Z)-N-isobutyl-2,6,8-decatrienamide;
2,3,5,6-tetramethoxyphenanthro[9,10:6',7']indolizidine;
5,7,8,15-Tetrahydro-3,4-dimethoxy-6-methylbenzo[e][1,3]dioxolo-[4,5-k][3]benzazecin-14(6H)-one;
(1S,6S,7R,8R,8aR)-Octahydro-indolizinetetrol;
(3S,4R)-Dihydro-3-[(R)-hydroxyphenylmethyl]-4-[(1-methyl-1H-imidazol-5-yl)methyl]-2(3H)-furanone;
(3S-cis)-3-Ethyldihydroxy-4-[(-methyl-1H-imidazol-5-yl)methyl]-2(3H)-furanone;
(S)-4-Ethyl-4-hydroxy-1H-pyrano[3'4':6,7]indolizino[1,2-b]quinoline-3,14(4H,12H)-dione;
1,2,3,4-Tetrahydro-6,7-dimethoxy-8-isoquinolinol;
1,2,3,4-Tetrahydro-6,7-dimethoxy-1-methyl-8-isoquinolinol;
N-(7S)-5,6,7,9-Tetrahydro-1,2,3,10-tetramethoxy-9-oxobenzo[a]heptalen-7-yl]acetamide;
1αH,5αH-tropan-3α-ol atropate;
1,2-(methylenedioxy)-6aβ-aporphin-11-ol;
(16α,17α)-17-Hydroxyyohimban-16-carboxylic acid methyl ester;
trans-8-methyl-N-vanillyl-6-nonenamide;
1,2-(methylenedioxy)aporphine;
(1R-trans)-2,3,5,7a-Tetrahydro-1-hydroxy-1H-pyrrolizine-7-methanol;
[1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;
(3α,14β,16α)-14,15-Dihydro-14-hydroxyeburnamenine-14-carboxylic acid methyl ester;
1,10-Dimethoxy-6aα-aporhine-2,9-diol;
6,7,12b,13-Tetrahydro-4H-bis[1,3]benzodioxolo[5,6-a:4',5'-g]quinolizine;
(8β)-8-methoxy-16-methyl-2,3:10,11-bis(methylenebis(oxy)]rheadan;
6',7',10,11-Tetramethoxyemetan;
3-(-Benzoyloxy)-8-methyl-8-azabicyclo[3.2.1]octane-2-carboxylic acid;
8,13,13b,14-Tetrahydro-14-methylindolo[2',3':3,4]pyrido[2,1-b]quinazolin-5(7H)-one;
6',12'-Dimethoxy-2,2'-dimethyl-6,7-[methylenebis(oxy)]oxyacanthan;
4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;
5,11-Dimethyl-6H-pyrido[4,-3b]carbazole;
6,7-Dihydro-1,2,3,10-tetramethoxy-7-(methylamino)benzo[a]heptalen-9(5H)-one;
(1α)-2,3-Didehydro-7-methoxycrinan-1-ol; and
(1α,3α)-7-methoxycrinan-1,3-diol.
Also disclosed is a compound in solid form, wherein the compound is:
N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one;
[1,α,3β(E),5α,6α,7α]-2-Methyl-2-butenoic acid-6,7-dihydroxy-8-methyl-8-azabicyclo[3.2.1]oct-3-yl ester;
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester;
(3aS-cis)-1,2,3,3a,8,8a-Hexahydro-1,3a,8-trimethylpyrrolo[2,3-b]indol-5-ol methylcarbamate(ester);
(1α,2β)-3,12-Dihehydro-9,10-[methylenebis(oxy)]galanthan-1,2-diol;
(3β,12α)-Solanid-5-ene-3,12-diol;
1-(6-methoxy-4-quinolyl)-3-(3-vinyl-4-piperidyl)-1-propanone;
(E,E,Z)-N-isobutyl-2,6,8-decatrienamide;
2,3,5,6-tetramethoxyphenanthro[9,10:6',7']indolizidine;
5,7,8,15-Tetrahydro-3,4-dimethoxy-6-methylbenzo[e][1,3]dioxolo[4,5-k][3]benzazecin-14(6H)-one;
(1S,6S,7R,8R,8aR)-Octahydro-indolizinetetrol;
(3S,4R)-Dihydro-3-[(R)-hydroxyphenylmethyl]-4-[(1-methyl-1H-imidazol-5-yl)methyl]-2(3H)-furanone;
(3S-cis)-3-Ethyldihydroxy-4-[(-methyl-1H-imidazol-5-yl)methyl]-2(3H)-furanone;
(S)-4-Ethyl-4-hydroxy-1H-pyrano[3'4':6,7]indolizino[1,2-b]quinoline-3,14(4H,12H)-dione;
1,2,3,4-Tetrahydro-6,7-dimethoxy-8-isoquinolinol;
1,2,3,4-Tetrahydro-6,7-dimethoxy-1-methyl-8-isoquinolinol;
N-(7S)-5,6,7,9-Tetrahydro-1,2,3,10-tetramethoxy-9-oxobenzo[a]heptalen-7-yl]acetamide;
1αH,5αH-tropan-3α-ol atropate;
1,2-(methylenedioxy)-6aβ-aporphin-11-ol;
(16α,17α)-17-Hydroxyyohimban-16-carboxylic acid methyl ester;
trans-8-methyl-N-vanillyl-6-nonenamide;
1,2-(methylenedioxy)aporphine;
(1R-trans)-2,3,5,7a-Tetrahydro-1-hydroxy-1H-pyrrolizine-7-methanol;
[1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;
(3α,14β,16α)-14,15-Dihydro-14-hydroxyeburnamenine-14-carboxylic acid methyl ester;
1,10-Dimethoxy-6aα-aporhine-2,9-diol;
6,7,12b,13-Tetrahydro-4H-bis[1,3]benzodioxolo[5,6-a:4',5'-g]quinolizine;
(8β)-8-methoxy-16-methyl-2,3:10,11-bis[methylenebis(oxy)]rheadan;
6',7',10,11-Tetramethoxyemetan;
3-(-Benzoyloxy)-8-methyl-8-azabicyclo[3.2.1]octane-2-carboxylic acid;
8,13,13b,14-Tetrahydro-14-methylindolo[2',3':3,4]pyrido[2,1-b]quinazolin-5(7H)-one;
6',12'-Dimethoxy-2,2'-dimethyl-6,7-[methylenebis(oxy)]oxyacanthan;
4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;
5,11-Dimethyl-6H-pyrido[4,-3b]carbazole;
6,7-Dihydro-1,2,3,10-tetramethoxy-7-(methylamino)benzo[a]heptalen-9(5H)-one;
(1α)-2,3-Didehydro-7-methoxycrinan-1-ol; or (1α,3α)-7-methoxycrinan-1,3-diol.

Any of the compositions disclosed herein may be substantially free of non-alkaloid plant material.

Any of the compositions disclosed herein may also be substantially free of plant material.

In an embodiment, any composition disclosed herein may be a pharmaceutical composition and the carrier may be a pharmaceutically acceptable carrier.

Also disclosed is a process for preparing any of the disclosed compounds or compositions containing them comprising isolating the compounds from one or more plant sources. Alternatively, the compounds may be synthesized by available synthesis techniques.

Further disclosed is a process for validating a batch of any of the compositions herein comprising obtaining a batch of the composition and determining if each alkaloid compound is present in the batch.

Also disclosed is a process for preparing a composition comprising obtaining an extract from a root of *Dovyalis abyssinica*, determining whether the extract has the alkaloid compounds N-Methyl-,L-tryptophan; 1,2-Methylenedioxy-9-hydroxy-10-methoxynoraporphine; 6-(1,2,3,4-Tetrahydro-6,7-dimethoxy-2-methyl-1-isoquinolinyl)furo[3,4-e]-1,3-benzodioxol-8(6H)-one; and [1,α,3β(E),5α,6α,7α]-2-Methyl-2-butenoic acid-6,7-dihydroxy-8-methyl-8-azabicyclo[3.2.1]oct-3-yl ester, and if so determined, formulating the composition.

Yet further disclosed is a process for preparing a composition comprising obtaining an extract from a root of *Clutia robusta*, determining whether the extract has the alkaloid compounds (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline; 3β-(Hydroxymethyl)-2α-methyl-4β-[(9-methyl-9H-pyrido[3,4-b]indol-1-yl)methyl]-2H-pyran-5-carboxylic acid methyl ester; or (3aS-cis)-1,2,3,3a,8,8a-Hexahydro-1,3a,8-trimethylpyrrolo[2,3-b]indol-5-ol methylcarbamate(ester), and if so determined, formulating the composition.

Additional embodiments of this invention include embodiments where the compounds disclosed herein are used in or made by the embodiments disclosed in U.S. Patent Application Publication No. 2007/0042053, the contents of which are incorporated by reference herein.

Definitions

For the purposes of this disclosure and unless otherwise specified, "a" or "an" means "one or more". All patents, applications, references and publications cited herein are incorporated by reference in their entirety to the same extent as if they were individually incorporated by reference.

As used herein, a person is considered HIV-negative if he/she has tested negative on the two-part HIV screening test (ELISA and Western blot).

As used herein, the term "therapeutically effective" or "effective amount" indicates that the materials or amount of material is effective to prevent, alleviate, or ameliorate one or more symptoms of a disease or medical condition, and/or to prolong the survival of the subject being treated.

As used herein, "pharmaceutically acceptable" indicates that the identified material does not have properties that would cause a reasonably prudent medical practitioner to avoid administration of the material to a subject, taking into consideration the disease or conditions to be treated and the respective route of administration.

"About" is used herein to mean in quantitative terms plus or minus 10%.

As used herein, amelioration of the symptoms of a particular disorder by administration of a particular pharmaceutical composition refers to any lessening, whether permanent or temporary, lasting or transient that can be attributed to or associated with administration of the composition.

As used herein, "combination" refers to any association between or among two or more items. The combination can be two or more separate items, such as two compositions or two collections. It can be a mixture thereof, such as a single mixture of the two or more items, or any variation thereof.

As used herein, "composition" refers to any mixture. It can be a solution, a suspension, liquid, powder, a paste, aqueous, non-aqueous or any combination thereof.

As used herein, "ingredient of a pharmaceutical composition" refers to one or more materials used in the manufacture of a pharmaceutical composition. Ingredient can refer to an active ingredient (an agent) or to other materials in the compositions. Ingredients can include water and other solvents, salts, buffers, surfactants, water, non-aqueous solvents, and flavorings.

As used herein, "pharmaceutical composition" refers a composition that contains an agent and one or more other ingredients i.e. a pharmaceutically acceptable carrier or excipient that is formulated for administration to a subject. An agent refers to an active ingredient of a pharmaceutical composition. Typically active ingredients are active for treatment of a disease or condition. For example, agents that can be included in pharmaceutical compositions include agents for treating infectious disease.

As used herein, "treatment" refers to any manner in which the symptoms of a condition, disorder or disease or other indication, are ameliorated or otherwise beneficially altered.

As used herein, "isolated" shall mean pure or substantially pure. Specifically, an "isolated" compound shall have a higher purity than an "extracted" compound and an isolated compound is therefore not the same as an extracted compound. In one embodiment, the compound is isolated to a purity of 85% or greater. In another embodiment, the compound is isolated to a purity of 90% or greater. In another embodiment, the compound is isolated to a purity of 95% or greater.

Thus this disclosure provides compounds having a purity range of 85% to 100%, where all integer unit amounts within this range are specifically disclosed as part of the invention. Thus, purity levels of 85%, 86%, 87%, 88% . . . 99%, and 100% are specifically included as embodiments of this invention.

"Free of plant material" as used herein means absent of any amount of materials of plant origin. Thus only compositions having synthetically produced compounds could be free of plant materials. Any compound isolated from a plant would always be accompanied by at least some trace amount of plant material.

As used herein, "substantially free of nonalkaloid plant material" shall mean a composition containing at least a trace amount of nonalkaloid plant material, but not more than a trace amount of such nonalkaloid plant material, and such composition can contain alkaloid plant material.

As used herein, "free of nonalkaloid plant material" shall mean a composition containing no nonalkaloid plant material, but such composition can contain alkaloid plant material.

As used herein, "synthesized alkaloid compounds" refers alkaloid compounds disclosed herein obtained by chemical synthesis.

As used herein, "CD4+ T cell" (or "T helper cell") refers to an immune T cell which is involved in protecting against infectious agents including viral, fungal and protozoal infectious agents. The CD4 molecule is expressed on the surface of T helper cells, which also serves as the primary target for HIV-1 and HIV-2. CD4 is the co-receptor for the T cell receptor and recruits the tyrosine kinase 1 ck intracellularly. CD4+ cell counts are reduced with the progression of HIV.

As used herein, "CD8+ T cell" refers to an immune T cell which has cytotoxic activity for infected cells. The CD8 molecule is expressed on the surface of T cytoxic lymphocytes. CD8 T-lymphocyte counts increase at the onset of HIV infection and continue to rise through the progression of the disease.

As used herein, "CD4+/CD8+ratio" refers to the ratio of CD4+ cells to CD8+ cells in a given sample, and is an important measure of disease progression.

As used herein, "cluster of differentiation" (CD) molecules are markers on the cell surface, as recognized by specific sets of antibodies, used to identify the cell type, stage of differentiation and activity of a cell.

As used herein, the terms "HIV" and "AIDS-related virus" mean the commonly designated HIV series (human immunodeficiency virus) and species thereof.

As used herein, the terms "HIV-related disease" and "AIDS-related disease" shall refer to any illness or syndrome, caused directly or indirectly by HIV or AIDS-related virus, including but not limited to infections whose source is fungal, viral and/or bacterial.

As used herein, "highly active antiretroviral therapy", or HAART, refers to treatment regimens designed to aggressively suppress viral replication and progress of HIV disease, usually consisting of three or more different drugs, such as for example, two nucleoside reverse transcriptase inhibitors and a protease inhibitors.

As used herein, "acute HIV infection" refers to the period of rapid viral replication immediately following exposure to HIV.

As used herein, "AIDS wasting syndrome" refers to the involuntary weight loss of 10 percent of baseline body weight plus either chronic diarrhea or chronic weakness and documented fever in the absence of a concurrent illness or condition other than HIV infection.

As used herein, "antiviral" refers to a substance or process that destroys a virus or suppresses replication (reproduction) of the virus.

As used herein, "viral load test" (in relation to HIV) refers to a test that measures the quantity of HIV RNA in the blood, expressed as number of copies per mL of blood plasma.

Discussion

This invention is based on our finding that certain combinations of certain plant material are effective treatments for infection. Based on our finding, the active compounds of each plant have been isolated. The following plant material was used: dried root of *Dovyalis abyssinica*, dried root of *Clutia robusta*, dried stem bark of *Prunus Africana*, dried stem bark of *Croton macrostachyus*, dried stem bark of *Acacia nilotica*, dried root of *Rhamnus prinoides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, and dried root of *Periploca linearifolia*. The preferred weight ratio of the aforementioned plant material is 2:2:2:2:2:2:1:2: 2:1:2:2:2:2, respectively, and each was chopped into small parts, dried and mixed into a herbal mixture. Other weight ratios can also be used.

The alkaloids specified in Table 1 were isolated from the plant material by first grinding each individual herb. Then, base was added to obtain an basic solution and said mixture was heated. Sufficient base is added to the defatted herbal material to achieve a pH of approximately 8. The concentration of the base added can be adjusted to provide sufficient liquid volume to cover the defatted herbal solid mixture. Any suitable base may be used, with preferred bases including NaOH, KOH, $Ca(OH)_2$, $Mg(OH)_2$, $NH_4OH$, and the like. The base extract is then heated for 2-4 hours. Preferably, the ingredients are slowly simmered under reflux conditions, although the same effect can be achieved by simmering the mixture in a covered pot.

Subsequently, acid was added to obtain an acidic solution, and said solution was heated. The acid was aqueous HCl and the pH of the acidic solution was about about 3. Preferably the acid is HCl, although other acids, including but not limited to, HBr, $HNO_3$, $H_2SO_4$, $H_3PO_4$, or any other acid suitable for achieving a pH of approximately 3 may be used as well. The concentration of the acid can be adjusted as necessary to provide sufficient volume to the mixture. The acidified solution is then boiled for approximately 2-4 hours under the same conditions employed for the heating of the basic solution. After heating, the mixture is cooled, and the aqueous layer is separated from the mixture, such as for example, by decanting the liquid from the remaining solids. Acid is then added to the remaining residue sufficient to achieve a pH of approximately 3, and the mixture is then reheated for approximately 2-4 hours under the same conditions previously employed. The aqueous layer is separated from the ingredients and the two acidified layers are combined. If necessary, additional acid extractions may be performed.

Then, the acidic solution was decanted to provide an acidic extract and a residue, acid was added to the residue and the acid and residue were heated at a simmer for about four hours. The acid was aqueous HCl. However, other extractive treatments, by heat or otherwise, could be used, and are within the scope of this invention.

Alkaloids were extracted from said acidic solution with a non-polar solvent, e.g. ether. Non-polar solvents are generally organic solvents having a dielectric constant less than 20. Non-polar solvents that may be used include, but are not limited to: alkanes, 1,4-dioxane, carbon tetrachloride, chloroform, methylene chloride, benzene, ethers, ethyl acetate, tetrahydrofuran, acetic acid, butanol, chlorobenzene, cycloalkanes, xylene, and the like. Preferred non-polar solvents are xylene and ether. The non-polar solvent added was about 20% by volume. However, other volume percentages could be used, and are within the scope of this invention.

The alkaloids were precipitated and collected at a pH of about 9 to isolate the alkaloids. However, other precepitative treatments, and/or other PH levels, could be used, and are within the scope of this invention.

The precipitated alkaloid mixtures from each of the 14 plants were subjected to repeated column chromatography. Silica gel was used as a stationary phase. However, other stationary phases could be used, and are within the scope of this invention. The column was first eluted with n-hexane, followed by varying proportions of ethyl acetate, until 100% ethyl acetate was added. The column was finally washed with methanol. Other elutants than n-hexane could be used, and could be followed by other compounds than ethyl acetate until different proportions were reached. The column was finally washed with methanol, although other washing agents could be used. The foregoing variations are within the scope of this invention.

Structures of each of the isolated alkaloids were elucidated using a combination of spectroscopic and physical data. Other methods of elucidation which are available now or which may come to be available in the future could be used, and are within the scope of this invention.

The isolated alkaloids are useful in the treatment of infection, such as for example, HIV and AIDS. As shown by the Examples set forth herein, extracts of the mentioned plant are an effective treatment of infections in subjects in need of such treatment. The alkaloid compounds in a plant are thought to be the active compounds in the plant. That is, the alkaloid compounds isolated from each plant described herein and in Table 1 below have at least analogous activity to the extracts.

Compounds and compositions disclosed herein may be prepared from plant material collected from the Mau Forest Complex in Western Kenya. Compositions prepared from aqueous extractions and purified extracts of plants from this region of Kenya exhibit increased potency in the treatment of infectious diseases. The Mau Forest Complex is located at 0° 30' South, 35° 20' East and in the Rift Valley Province, and spans four Kenyan administrative districts: Narok, Nakuru, Bomet and Kericho. Mean annual rainfall varies from 1000 to 1500 mm with peaks in April and August. The rainfall pattern at the western flanks is governed by the moist monsoon winds from the Indian Ocean and dry winds from the Great Rift Valley. The western flanks of the Mau Forest Complex are influenced by the Lake Victoria macroclimatic region and are generally wetter with annual rainfall greater than 2000 mm and more evenly distributed. Mean annual temperatures for the Mau Forest Complex range from 12-16° C. The soil of the Mau Forest Complex is rich volcanic loam having a pH between 3.8-5.8.

The vegetational pattern follows an altitudinal gradient with local topographical ecolines. The closed canopy moist mountain forest at lower altitudes becomes increasingly intermixed with bamboo from 2200 m onwards. Between 2300 and 2500 m, pure bamboo (*Arundinaria alpina*) swards are found. Above 2500 m this gives way to mixed bamboo/tree stands, both associated with grass clearings that usually represent a sub-climax resulting from burning and cutting of bamboo. A marginal type of mountain sclerophyll forest, wherein the plants generally have hard leaves to prevent wilting during dry conditions, occupies the highest altitudes of the Mau complex.

Plants in the Western flank of the Mau Forest Complex have shown the highest potency for the herbal compositions. Plants growing in the Western flank, (which is generally a high rainfall, high altitude region), have fewer environmental stresses. It is therefore possible that plants of the Western flank have more biosynthetic pathways, which may in turn lead to the production of a greater number of diverse compounds, which may in turn explain the greater potency of plants from the Western flank (as compared to other regions of the Mau Forest Complex). Alternatively, the greater potency plant extracts from the Western flank plants may be a result of a greater variety and number of alkaloids and other compounds in the plant extracts, such that the combined effect is greater than the sum of their individual effects.

The East Mau Forest Complex has a drier vegetation of Cedar and Podo. Wherever these species have been extracted, colonizing species such as *Neuboutonia marcrocalyx* and *Macaranga capensis* can be found.

The compounds and compositions disclosed herein may be prepared using plants collected from three altitude ranges of the Mau Forest Complex: 2000 m (annual rainfall of 1000 mm), 2300 m (1500 mm), 2500 m (western Mau flank, annual rainfall greater than 2000 mm) above sea level. The Western flanks of the Mau Forest contain plants that are particularly preferred for preparing the herbal compositions of the invention. The plants grown in the drier Eastern flank of the Mau Forest Complex also may be used.

Plant material for preparing compositions of the invention may also be obtained from plants grown in a greenhouse environment. The germination of the seeds of particular plants may be altitude or soil dependent. Seeds for greenhouse planting may require collection from the natural dispersal agents as they exist in the wild. Additionally, simulation of rainfall, sunlight (an average of 12 hours per day in the Mau Forest Complex), and soil conditions of the Mau Forest Complex (i.e., rich volcanic loam having a pH between 3.8-5.8) may be required to obtain plants of similar potency.

The seeds of *Dovyalis abyssinica* (representative seed of said line having been deposited under ATCC Accession No. PTA-6969) are contained in a fleshy fruit. There are about 4 seeds enclosed by the flesh. A ripe fleshy fruit can be soaked in water for about 4 days, to make it possible to squeeze with minimum force to release the small seeds, each being approximately the size of a tomato seed or slightly larger. The seeds are then washed, dried and stored, awaiting germination under Mau Forest-like environmental conditions. In the wild, the fruit flesh is soaked by rain water, which results in the release of the seeds. The seeds grow naturally under the environmental conditions of the Mau Forest Complex as described above.

The *Clutia robusta* (representative seed of said line having been deposited under ATCC Accession No. PTA-6970) seeds are much smaller and encased in berries having a nut-like outer covering which encases approximately 3 to 4 seeds the size of a grain of sand. When mature seeds are exposed direct sunlight, they disperse rapidly in a process called explosive dispersal. This is not a problem in the wild, but if one is interested in collecting the seeds, care and intelligence are required, or else all the seeds will fly away under the scattering effect of the hot sun.

To recover the *Clutia robusta* seeds, the berries should be placed in a metallic container, and covered with a material that allows sunlight to enter, such as a transparent polyethylene film surrounding a container of appropriate wire mesh. Exposure to light will cause the shells to break open, releasing the seeds which can then be separated from the chaff.

The optimal time for planting the *Clutia* and *Dovyallis* seeds in their natural environment is during the long rains, typically around the month of April. However, in the wild, the plants will generally grow throughout the year, except during the dry season, as the plants require a considerable amount of water and light to grow.

*Croton macrostachyus* (representative seed of said line have been deposited with the ATCC, but successfully germinated by the ATCC) produces pale pea-sized capsules, on drooping spikes to 30 cm long, splitting open on the tree to release 3 shiny grey seeds, covered at one end by a soft, creamy aril, or envelope.

*Prunus Africana* (representative seed of said line have been deposited with the ATCC, but successfully germinated by the ATCC) produces spherical fruit, about 10 mm in diameter and is pinkish brown in color.

The *Acacia nilotica* (representative seed of said line having been deposited under ATCC Accession No. PTA-7378) plant produces straight or curved pods measuring approximately 17×2 cm. When young, the pods are green and fleshy but get darker with age, and are usually velvety. Pods have a fruity odor and open on the ground to release seeds.

*Ekebergia capensis* (representative seed of said line have been deposited with the ATCC, but successfully germinated by the ATCC) produces rounded, thin skinned berries, up to 2.5 cm in diameter, on long stalks in heavy bunches, which are yellow to red in color when mature.

The berry-like fruits of *Rhamnus prinoides* (representative seed of said line have been deposited with the ATCC, but successfully germinated by the ATCC) are approximately the size of a pea (about 5 mm in diameter), roundish and clearly divided into three compartments. They are fleshy and green, turning red and then purple as they ripen.

The fruit of the *Asparagus africanus* (representative seed of said line have been deposited with the ATCC, but successfully germinated by the ATCC) is a round berry, approximately 0.5 cm in diameter, green aging to orange, found most of the year. It is spread mainly by birds carrying the seeds.

*Anthocleista grandiflora* (representative seed of said line have been deposited with the ATCC, but successfully germinated by the ATCC) produces fruits that are oval in shape, measuring approximately 3 cm×2 cm, glossy, smooth and brown when mature. Multi-seeded, large fruits are found throughout the year.

*Bersama abyssinica* (representative seed of said line have been deposited with the ATCC, but successfully germinated by the ATCC) produces a smooth, spherical capsule, measuring approximately 2.5 cm in diameter, golden velvety at first, losing most of the hair and becoming brown by maturity; splitting into four valves to reveal attractive bright red seeds, about 10 mm long, enveloped for about their half length by a yellow, cup-shaped aril.

*Adenia gummifera* (representative seed of said line have been deposited with the ATCC, but successfully germinated by the ATCC) produces a fruit which is a stalked 3-valved capsule, leathery or fleshy, often red; seeds compressed with bony testa in a fleshy aril.

*Plantago palmata* (representative seed of said line having been deposited under ATCC Accession No. PTA-7377) produces a capsule-like fruit with two seeds per capsule.

*Periploca linearifolia* (representative seed of said line having been deposited under ATCC Accession No. PTA-7375) produces black seeds measuring approximately 10 mm long and 2 mm wide with white wool measuring around 3 cm attached to the tips of the seeds. The seeds are enclosed in pods measuring about 12 cm long. Upon maturity, the pods break open upon exposure to sunlight. This releases the seeds, which are borne aloft by the wool as they are dispersed by wind. Alternatively, these plants may be cultivated from stem cuttings, which when laid on or planted in the ground, grow roots and propagate new plants.

*Clematis hirsuta* (representative seed of said line having been deposited under ATCC Accession No. PTA-7383) produces yellowish seeds measuring approximately 3 mm in length and 1 mm in breadth. The seeds are surrounded by yellowish-white wool which measures about 5 mm long. The wool carries the seeds upon the wind, which is the dispersal agent.

HIV Testing

As noted previously, for purposes of this application, a person is considered HIV-negative if the subject tested negative on a two-part HIV screening tests, consisting of an initial screening test and a confirmatory test.

An infected individual usually goes for testing for one or more of the following reasons: 1) the individual feels ill, 2) the individual's sexual partner is ill and has tested positive, 3) the individual's sexual partner died of AIDS; or 4) the individual suspects his/her sexual partner is sexually promiscuous.

The initial screening test is ELISA (Enzyme-Linked Immunosorbent Assay), an enzyme immunoassay (EIA) to determine the presence of HIV antibodies. The ELISA test uses artificial HIV proteins that capture antibodies to the virus and is more than 99 percent accurate. If antibodies to HIV are present (positive result), the test is typically repeated. However, other antibodies can cause a false-positive result.

Generally, HIV-1 antibodies are detectable approximately 25 days after acute infection, with nearly all infected subjects testing HIV positive 12 weeks after infection. The process of developing antibodies to a virus is termed seroconversion, and individuals who become antibody-positive are often called seroconverters.

Two types of HIV have been identified: HIV-1 and HIV-2, of which, HIV-1 is more common. HIV-1 and HIV-2 are similar in the modes of transmission (sexual contact, sharing needles, etc.) and infected individuals are generally subject to the same opportunistic infections. However, HIV-2 appears to weaken the immune system more slowly than HIV-1.

In Kenya, individuals are generally tested for antibodies to both HIV-1 and HIV-2. HIV-1 is generally more common in the Western world and HIV-2 is more common in Africa. In Kenya however, most HIV-positive individuals have the HIV-1 infection. It is believed that 90% of the HIV-positive cases in Kenya are HIV-1, with the remaining 10% of HIV-positive cases being the HIV-2. While rare, subjects occasionally are HIV antibody-positive to both types of HIV (i.e. HIV-1 and HIV-2).

The second part of the HIV screening test is called the confirmatory test. In the U.S., the most often used confirmatory test is the Western blot, wherein an electrical field is used to separate the various components by their molecular weight prior to evaluating antibody binding. This allows identification of antibodies to specific viral antigens, which show up as identifiable "bands" on a strip of test paper. The Western blot test is more difficult to perform and accurately interpret than the ELISA test, but it is less likely to give a false-positive result because it can distinguish HIV antibodies from other antibodies that may react to the ELISA. Other confirmatory tests may be used, including the indirect fluorescent antibody assay (IFA) and the radioimmunoprecipitation assay (RIPA).

One major drawback of antibody tests is the "window" period (i.e. the time it takes the body to produce antibodies after infection has begun). The screening tests do not correlate to the presence or absence of symptoms. The standard HIV tests do not detect the virus itself, but instead detect the antibodies that the body produces in response to the virus. During the period before the antibodies are produced, a person may be infected with HIV and can infect others, and still test negative on the HIV antibody test. It is therefore important to tell subjects who test negative to avoid engaging in high-risk behavior and to return for retesting at a later date.

The p24 antigen test can be used in diagnosing HIV early in the course of infection. It is primarily used to screen the blood supply but in some places it is used for testing for HIV. The p24 antigen is a protein that is part of the HIV. Early in the infection, it is produced in excess and can be detected in the blood serum by a commercial test. The p24 test can detect HIV infection before the HIV antibody test can and it is recommended 2-3 weeks after a risk exposure.

Individuals that test positive for HIV are regularly administered two tests to monitor HIV levels in the blood and to determine how the virus is affecting the immune system. These tests are: (1) a viral load measurement, and (2) CD4+ cell counts.

Viral load measurement (also called the HIV plasma RNA test) determines how many HIV viral particles are present in a given amount of a person's blood. Test results help determine the best treatment for the HIV infection as the viral load test shows how fast the virus is multiplying in the body. Because HIV reproduces by making copies of itself, the results are given as copies per milliliter (mL). Viral load testing can also reveal the presence HIV infection before antibodies can be detected and can also accurately determine whether a baby born to an infected mother has HIV.

CD4+ cell counts (T-lymphocyte measurements) provide an estimate of the immunologic status of an individual and help determine the immediate risk of opportunistic infection. The CD4+ count measures the number of a certain type of white blood cell that is most affected by HIV, and are measured every 3 to 4 months in individuals infected with HIV. On average, an individual infected with HIV loses approximately, 30-60 CD4+ cells per year, although in some subjects, CD4+ T-lymphocyte counts may remain stable for years followed by rapid decline.

CD4(T4) or CD4+ cells are a type of T cell involved in protecting against infections, such as for example, viral, fungal, and protozoal infections. Destruction of these cells is the major cause of immunodeficiency observed in AIDS, and decreasing CD4+ lymphocyte counts appear to be the best indicator for the potential development of opportunistic infections. In judging the severity of HIV/AIDS cases, the CD4+ lymphocyte count is more indicative of the severity of the disease than gross symptomalogy, although it is also true that certain symptoms may be associated with particular CD4+ lymphocyte levels. See, for example, FIG. 1. Average normal adult CD4+ cell counts typically ranges from 500 to 1,500/2,000 cells per cubic milliliter of blood.

As CD4+ cell counts decrease below the normal adult levels during primary HIV infection, CD8+ or cytotoxic T-lymphocytes also increase. However, most studies indicate that an increase in CD8 count is not a prognostic indicator of disease progression. Some clinicians in the U.S. use the CD4/CD8 ratio as an indicator of disease progression, however, this ratio varies not only with the severity of the disease, but with the ethnicity of the subject.

There are several systems for classifying and staging HIV infection. The most commonly-used system is the CDC (Centers for Disease Control) Scheme. The CDC scheme has three classifications based upon CD4 counts. The definitions of the three CD4+ T-lymphocyte categories I as follow: Category 1: >500 cells/mm.sup.3 (or CD4%>28%); Category 2: 200-499 cells/mm$^3$ (or CD4% 14%-28%); and Category 3: <200 cells/mm$^3$ (or CD4%<14%)

In addition to the CDC classification scheme, there are also 3 possible categories of clinical conditions, which are designated by the letters A, B and C. Therefore, a given individual can have the following CDC classification and clinical categorization designation: 1-A, or 1-B, or I-C, 2-A, 2-B, 2-C, 3-A, 3-B or 3-C.

An individual in category A is identified as an adolescent or adult (>13 years) with documented HIV infection having one or more of the following conditions (and lacking any of the conditions associated with categories B and C): asymptomatic HIV infection; persistent generalized lymphadenopathy; and acute (primary) HIV infection with accompanying illness or history of acute HIV infection.

An individual in category B is identified as an adolescent or adult (>13 years) with documented HIV infection having one or more of the following conditions (and lacking any of the conditions associated with category C) and that meet at least one of the following criteria: (a) the conditions are attributed to HIV infection or are indicative of a defect in cell-mediated immunity; or (b) the conditions are considered by physicians to have a clinical course or to require management that is complicated by HIV infection. Examples of conditions in clinical category B include but are not limited to: bacillary angiomatosis; candidiasis (oropharyngeal, i.e. thrush); candidiasis (vulvovaginal, persistent, frequent, or poorly responsive to therapy); cervical dysplasia (moderate or severe/cervical carcinoma in situ); constitutional symptoms, such as fever (body temperature of 38.5° C. or greater) or diarrhea lasting longer than 1 month; hairy leukoplakia (oral); herpes zoster (shingles), involving at least two distinct episodes or more than one dermatome; idiopathic thrombocytopenic purpura; listeriosis; pelvic inflammatory disease (particularly if complicated by tubo-ovarian abscess); and (11) peripheral neuropathy. For classification purposes, Category B conditions take precedence over Category A conditions. For example, an individual previously treated for oral or persistent vaginal candidiasis (but not exhibiting a Category C disease or condition) who is now asymptomatic, should be classified in Category B.

An individual in category C is identified as an adolescent or adult (>13 years) with documented HIV infection having one or more of the following conditions Category C conditions include the following: candidiasis of bronchi, trachea, or lungs; candidiasis (esophageal); invasive cervical cancer; coccidioidomycosis (disseminated or extrapulmonary); cryptococcosis (extrapulmonary); cryptosporidiosis (chronic intestinal, greater than 1 month's duration); cytomegalovirus disease (other than liver, spleen, or nodes); cytomegalovirus retinitis (with loss of vision); encephalopathy (HIV-related); herpes simplex: chronic ulcer(s) (greater than 1 month's duration), or bronchitis, pneumonitis, or esophagitis; histoplasmosis (disseminated or extrapulmonary); isosporiasis (chronic intestinal, greater than 1 month's duration); Kaposi's sarcoma; lymphoma (Burkitt's, or equivalent term), lymphoma, (immunoblastic, or equivalent term); Lymphoma (primary, of brain); mycobacterium avium complex or M. kansasii, disseminated or extrapulmonary; mycobacterium tuberculosis, (any site, pulmonary or extrapulmonary); mycobacterium, (other species or unidentified species, disseminated or extrapulmonary); *pneumocystis carinii* pneumonia; pneumonia (recurrent); progressive multifocal leukoencephalopathy; *Salmonella septicemia* (recurrent); toxoplasmosis of brain; and wasting syndrome due to HIV. For classification purposes, once a Category C condition has occurred, the individual will remain in Category C.

One method of treatment for HIV-positive individuals is the highly active antiretroviral therapy (HAART) regimen. HAART is a therapeutic treatment regime consisting of the combination of anti-HIV drugs, that is prescribed to HIV-positive individuals even before they develop symptoms of AIDS. The therapy usually includes one nucleoside analog, one protease inhibitor and either a second nucleoside analog or a non-nucleoside reverse transcription inhibitor (NNRTI). Frequently, the HAART regime is toxic to the individual, resulting in adverse side effects. For example, HAART can be toxic to blood because it almost always includes one or two nucleoside analogs, like AZT that are notorious for their toxicity to red and white blood cells and blood cell production. Various forms of anemia are very common and sometimes are irreversible. However, it is extremely rare for a subject on the HAART regimen reverse his/her HIV status in Kenya.

Examples of drugs administered for the HAART treatment regime include: azidovudine (AZT), didanosine (dideoxyinosine, ddI), zalcitabine (dideoxycytosine, ddC), lamivudine (epivir, 3TC), nevirapine (Viramune), abacavir (Ziagen), stavudine (Zerit, d4T), tenofovir (Viread), efavirenz (Sustiva), amprenavir (Agenerase), lopinavir (Kaletra), nefinavir (Viracept), saquinavir (Invirase), ritonavir (Norvir), indinavir (Crixivan), and delavirdine (Rescriptor).

In another aspect, pharmaceutical compositions of the above listed compounds are provided. For example, the pharmaceutical composition may be provided as a beverage, a capsule, a tablet, a powder, a candy, a gel, or a nutritional product. The compounds may be further mixed with excipients as are known to those of skill in the art, some of which are listed in "Remingtons Pharmaceutical Sciences," Mack Pub. Co., New Jersey (1991), which is incorporated herein by reference.

Where control of the herbal pharmaceutical composition is desired, rationing may be imposed. For example, patients (i.e. subjects) receiving the compositions may be supplied with an amount of the composition as is necessary for one week. This will allow for even rationing and to prevent the subject or patient from sharing of the preparation with others, which would be in contravention of the dosage directions.

The compounds and compositions disclosed herein are isolated from the roots of *Dovyalis abyssinica* and *Clutia robusta*, and optionally one or more of the following: the stem bark of *Prunus Africana*, stem bark of *Croton macrostachyus*, stem bark of *Acacia nilotica*, roots of *Rhamnus prinoides*, roots of *Adenia gummifera*, roots of *Asparagus africanus*, stem bark of *Anthocleista grandiflora*, whole plant of *Plantago palmata*, roots of *Clematis hirsuta*, stem bark of *Ekebergia capensis*, stem bark of *Bersama abyssinica*, and roots of *Periploca linearifolia*. Preferably, the ingredients collected are fresh, although dried samples may also be used.

The ingredients are combined and chopped into small pieces and dried. The compounds can be used in the following weight ratio, by reference to the plant from which they are isolated: *Dovyalis abyssinica, Clutia robusta, Prunus Africana, Croton macrostachyus, Acacia nilotica, Rhamnus prunioides, Adenia gummifera, Asparagus africanus, Anthocleista grandiflora, Plantago palmata, Clematis hirsuta, Ekebergia capensis, Bersama abyssinica* and *Periploca linearifolia*, in a weight ratio of 2:2:2:2:2:2:1:2:2:1:2:2:2:2, respectively.

A number of the individual compounds of the alkaloid mixtures have been characterized by methods known to those of skill in the art. For example, spectroscopic and analytical characterizations were used to identify the compounds. Table 1 lists the plant species, identified compounds, and the corresponding chemical structures of the compounds.

TABLE 1

Specific Alkaloids present in each plant

| Plant Species | Chemical Name | Structure |
|---|---|---|
| *Dovyalis abyssinica* | N-Methyl-L-tryptophan | 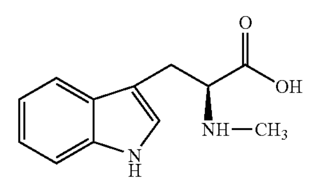 |
| | 1,2-Methylenedioxy-9-hydroxy-10-methoxynoraporphine | |
| | 6-(1,2,3,4-Tetrahydro-6,7-dimethoxy-2-methyl-1-isoquinolinyl)furo[3,4-e]-1,3-benzodioxol-8(6H)-one | |

TABLE 1-continued

Specific Alkaloids present in each plant

| Plant Species | Chemical Name | Structure |
|---|---|---|
| | [1,α,3β(E),5α,6α,7α]-2-Methyl-2-butenoic acid-6,7-dihydroxy-8-methyl-8-azabicyclo[3.2.1]oct-3-yl ester. | |
| Clutia robusta | (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline | 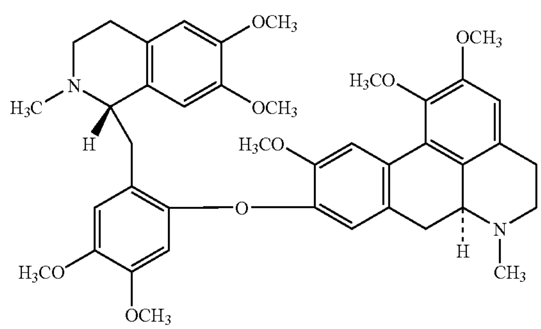 |
| | 3β-(Hydroxymethyl)-2α-methyl-4β-[(9-methyl-9H-pyrido[3,4-b]indol-1-yl)methyl]-2H-pyran-5-carboxylic acid methyl ester | |
| | (3aS-cis)-1,2,3,3a,8,8a-Hexahydro-1,3a,8-trimethylpyrrolo[2,3-b]indol-5-ol methylcarbamate (ester). | |
| Acacia nilotica | (1α,2β)-3,12-Dihehydro-9,10-[methylenebis(oxy)]galanthan-1,2-diol; | 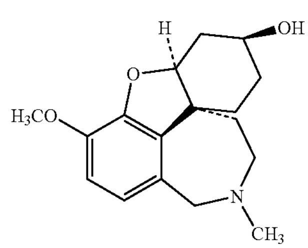 |

TABLE 1-continued

Specific Alkaloids present in each plant

| Plant Species | Chemical Name | Structure |
|---|---|---|
| | (3β,12α)-Solanid-5-ene-3,12-diol | |
| | 1-(6-methoxy-4-quinolyl)-3-(3-vinyl-4-piperidyl)-1-propanone; and | |
| | (E,E,Z)-N-isobutyl-2,6,8-decatrienamide | |
| *Bersama abyssinica* | 2,3,5,6-tetramethoxyphenanthro-[9,10:6',7']indolizidine | 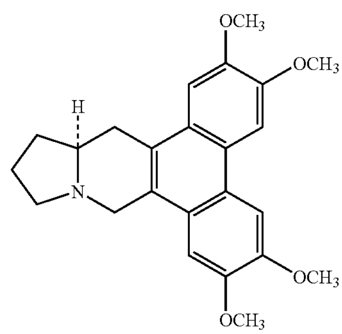 |
| | 5,7,8,15-Tetrahydro-3,4-dimethoxy-6-methylbenzo[e][1,3]dioxolo[4,5-k][3]benzazecin-14(6H)-one | |
| | (1S,6S,7R,8R,8aR)-Octahydro-indolizinetetrol | |
| *Clematis hirsute* | (3S,4R)-Dihydro-3-[(R)-hydroxyphenylmethyl]-4-[(1-methyl-1H-imidazol-5-yl)methyl]-2(3H)-furanone | 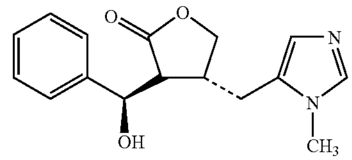 |

TABLE 1-continued

Specific Alkaloids present in each plant

| Plant Species | Chemical Name | Structure |
|---|---|---|
| | (3S-cis)-3-Ethyldihydroxy-4-[(-methyl-1H-imidazol-5-yl)methyl]-2(3H)-furanone | |
| Plantago palmate | (S)-4-Ethyl-4-hydroxy-1H-pyrano[3'4':6,7]indolizino[1,2-b]quinoline-3,14(4H, 12H)-dione | 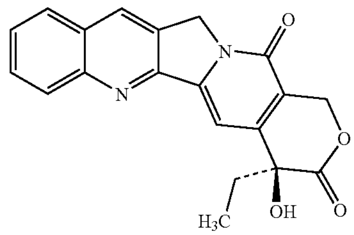 |
| | 1,2,3,4-Tetrahydro-6,7-dimethoxy-8-isoquinolinol | |
| | 1,2,3,4-Tetrahydro-6,7-dimethoxy-1-methyl-8-isoquinolinol | |
| | N-(7S)-5,6,7,9-Tetrahydro-1,2,3,10-tetramethoxy-9-oxobenzo[a]heptalen-7-yl]acetamide | |
| Rhamnus prinoides | 1αH,5αH-tropan-3α-ol atropate | 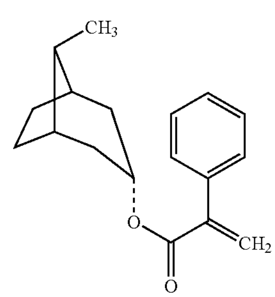 |

TABLE 1-continued

Specific Alkaloids present in each plant

| Plant Species | Chemical Name | Structure |
|---|---|---|
| | 1,2-(methylenedioxy)-6aβ-aporphin-11-ol | |
| Croton macrostachyus | (16α, 17α)-17-Hydroxyyohimban-16-carboxylic acid methyl ester | 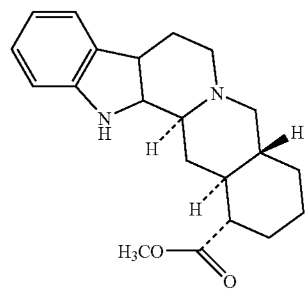 |
| | trans-8-methyl-N-vanillyl-6-nonenamide | |
| | 1,2-(methylenedioxy)aporphine | |
| | (1R-trans)-2,3,5,7a-Tetrahydro-1-hydroxy-1H-pyrrolizine-7-methan | |
| | [1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester | |

TABLE 1-continued

Specific Alkaloids present in each plant

| Plant Species | Chemical Name | Structure |
| --- | --- | --- |
| *Asparagus africanus* | (3α,14β,16α)-14,15-Dihydro-14-hydroxyeburnamenine-14-carboxylic acid methyl ester | 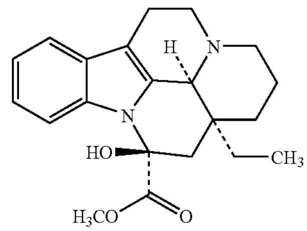 |
| | 1,10-Dimethoxy-6aα-aporhine-2,9-diol | |
| *Ekebergia capensis* | 6,7,12b,13-Tetrahydro-4H-bis[1,3]benzodioxolo[5,6-a:4',5'-g]quinolizine | 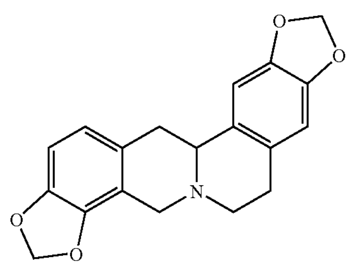 |
| | (8β)-8-methoxy-16-methyl-2,3:10,11-bis[methylenebis(oxy)]rheadan | |
| *Anthocleista grandiflora* | 6',7',10,11-Tetramethoxyemetan | 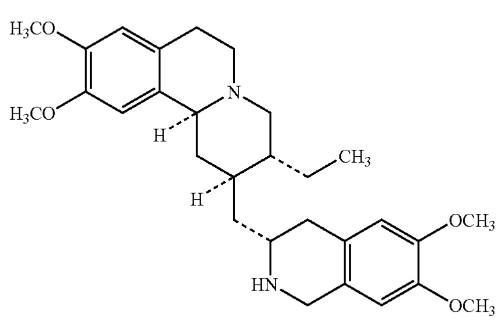 |

TABLE 1-continued

Specific Alkaloids present in each plant

| Plant Species | Chemical Name | Structure |
|---|---|---|
| | 3-(-Benzoyloxy)-8-methyl-8-azabicyclo[3.2.1]octane-2-carboxylic acid | |
| *Adenia gummifera* | 8,13,13b,14-Tetrahydro-14-methylindolo[2',3':3,4]pyrido-[2,1-b]quinazolin-5(7H)-one | 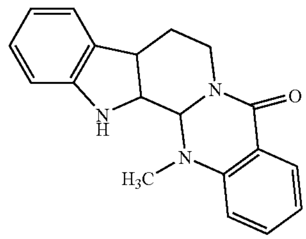 |
| | 6',12'-Dimethoxy-2,2'-dimethyl-6,7-[methylenebis(oxy)]-oxyacanthan | |
| *Periploca linearifolia* | 4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol | 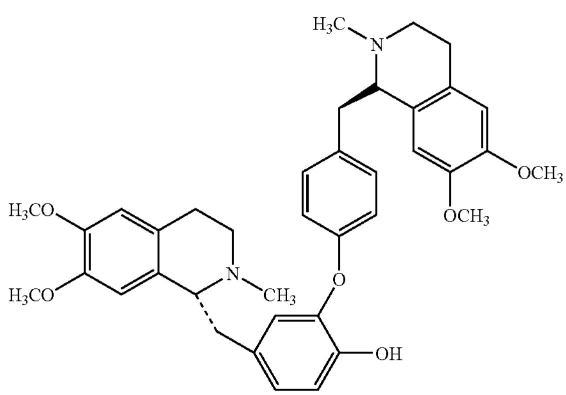 |
| | 5,11-Dimethyl-6H-pyrido[4,-3b]carbazole | |

TABLE 1-continued

Specific Alkaloids present in each plant

| Plant Species | Chemical Name | Structure |
|---|---|---|
| | 6,7-Dihydro-1,2,3,10-tetramethoxy-7-(methylamino)benzo[a]heptalen-9(5H)-one | |
| *Prunus Africana* | (1α)-2,3-Didehydro-7-methoxycrinan-1-ol | 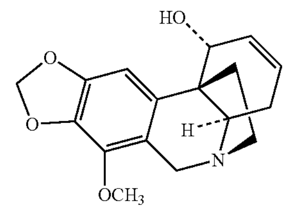 |
| | (1α,3α)-7-methoxycrinan-1,3-diol | |

The invention will now be described in greater detail by reference to the following non-limiting examples.

EXAMPLES

Determination of Bioactivity of Compositions having the disclosed compounds.

The efficacy of compositions having the disclosed compounds were tested against *Escherichia coli* (*E. coli*) and *Staphylococcus aureus* (*S. aureus*). The specific compositions were in the form of plant extracts. Solutions containing 100 ppm (parts per million) of each plant extract were prepared for use in the anti-bacterial assay.

Preparation of bacterial culture of *E. coli* and *S. aureus*.

Standard cultures of *E. coli* (representing gram-negative strains of bacteria) and *S. aureus* (representing gram-positive bacteria) were obtained from Moi University Teaching and Referral Hospital. Assays were conducted at the Moi University Department of Botany.

Nutrient agar was used as growth medium for both bacteria samples. The agar was sterilized in an autoclave at 120° C., cooled and poured into sterile Petri dishes and allowed to set. Sterile conditions were achieved and maintained by exposing the area to a UV lamp during sample preparation and the assay the procedure.

The cooled agar medium was streaked on the surface with each bacteria culture. "Wells" were dug in the middle of the medium, using a cork borer, where the prepared plant extract was deposited. A control experiment was also performed, using plain sterile water in place of the plant extracts.

Cultures were incubated for 12 hours, after which zones of inhibition of bacterial growth were determined and measured. Bacteria-growth inhibition was expressed in diameters (mm), and was determined by measuring the distance from edge of the well to area where the bacteria begin to show growth. Generally, the larger inhibition diameter indicates greater potency of the particular extract against the bacteria.

Of the 23 plants which were screened in this assay, 14 of the plants had bacteria growth inhibition diameters greater than 8 mm, which was previously determined to be the minimum activity required for adoption of the extract for the herbal remedy. The anti-bacterial activities of the plants were compared with standard antibiotics. Of the 14 plants having inhibition diameters greater than 8 mm, *Dovyalis abyssinica* and *Clutia robusta* demonstrated the greatest anti-bacterial activity. Results for plant extracts exhibiting inhibition diameters greater than 8 mm are provided in the Table 2.

TABLE 2

Inhibition Diameters
Zones of Inhibition Expressed as Inhibition Diameter (mm)

| | Plant Name | *E. coli* | *S. aureus* |
|---|---|---|---|
| 1 | *Dovyalis abyssinica* | 17.2 | 16.6 |
| 2 | *Clutia robusta* | 16.7 | 15.8 |
| 3 | *Prunus Africana* | 14.7 | 14.6 |
| 4 | *Croton macrostachyus* | 14.7 | 14.4 |
| 5 | *Acacia nilotica* | 13.6 | 13.2 |
| 6 | *Ekebergia capensis* | 12.8 | 13.0 |
| 7 | *Clematis hirsuta* | 11.9 | 12.8 |
| 8 | *Adenia gummifera* | 11.7 | 12.8 |
| 9 | *Asparagus africanus* | 11.3 | 11.2 |
| 10 | *Plantago palmata* | 11.0 | 11.0 |

TABLE 2-continued

Inhibition Diameters
Zones of Inhibition Expressed as Inhibition Diameter (mm)

|  | Plant Name | E. coli | S. aureus |
|---|---|---|---|
| 11 | Rhamnus prinoides | 10.9 | 10.8 |
| 12 | Periploca linearifolia | 10.9 | 10.6 |
| 13 | Bersama abyssinica | 10.5 | 10.3 |
| 14 | Anthocleista grandiflora | 10.0 | 9.7 |

Administration of the Composition

The plant extract precipitates are preferably purified and collected in either crystalline, paste or powder form. The precipitates can administered to a subject as a beverage, capsule, tablet, powder, candy, gel, nutritional product or pharmaceutical product. The amounts for administration may vary and may be readily determined by those of skill in the art. For example, the amount may be from 0 to about 50 grams, from about 0.5 grams to about 35 grams, from about 0.1 and 25 grams, from about 0.1 to about 10 grams, or from about 0.1 grams to about 5 grams of alkaloids, in whatever composition form, are administered per day to an infected subject. In one non-limiting example, the herbal composition is administered as a beverage wherein approximately 1 tbsp of powdered extract is dissolved in approximately 250 mL of hot water, and drunk. Other amounts and volumes will be recognized by those of skill in the art. Dosing is either twice daily at 12 hour intervals, or three times daily at eight hour intervals (depending on the level of infection of the test subject), and is preferably administered with a meal.

Subjects in the current trials were screened at the Walter Reed Hospital of the U.S. Army in Kericho, Kenya, the Moi University Hospital in Eldoret, and at various Voluntary Counseling and Testing (VCT) Centers scattered throughout the country.

Subjects° CD4 and CD8 counts were measured using a FACSCount™ system following procedures provided in the FACSCount White Paper (July 1994). HIV-1 and HIV-2 antibodies were detected using a bioMerieux Vironostika® HIV Uni-Form II Ag/Ab ELISA system.

All subjects administered the herbal composition were HIV-positive adults. Prior to administration of the herbal composition, an initial CD4 count for each subject was determined, followed by an assessment of the level of opportunistic infections. Those with fewer opportunistic infections were administered the herbal composition twice daily after meals, at twelve hour intervals. Those with more opportunistic infections were administered the herbal composition three times daily, at 8 hours intervals. Each subject was given one week's dosage during each visit to the clinic. This was done to make it possible to monitor compliance, and to avoid the possibility of subjects sharing the drug with others.

Example 1

Initial studies for the treatment of HIV positive subjects with herbal remedy were conducted by treating four HIV positive subjects with two different herbal remedies. Two subjects were administered a herbal composition which included the extract of *Dovyalis abyssinica*, while the other two subjects were administered a herbal remedy which included the extract of *Clutia robusta*. The subjects were each treated for a period of three months. The CD4 counts of both sets of subjects (i.e., those administered either *Dovyalis abyssinica* or *Clutia robusta*) increased by approximately 10 per month of treatment.

Example 2

In another study, three subjects were administered a herbal composition prepared with a 1:1 ratio by weight mixture of *Dovyalis abyssinica* and *Clutia robusta* for a period of approximately three months. The CD4 counts of the subjects treated with the mixture increased by approximately 30 per month.

Example 3

In yet another experiment, 21 subjects were administered a herbal composition containing extracts of *Dovyalis abyssinica, Clutia robusta, Prunus Africana, Croton macrostachyus, Acacia nilotica, Ekebergia capensis, Clematis hirsute* and *Adenia gummifera*. The 8 plant extracts were selected from 23 total plant extracts which had been previously assayed against *E. coli* and *S. aureus*. As shown in Table 3, CD4 counts of subjects increased by up to 100 per month, but none of the subjects tested HIV negative within the three-month period.

TABLE 3

CD4 Counts per Month

| Subject ID | $CD_{4/ul}$ per month | | | | |
|---|---|---|---|---|---|
|  | Month 1 | Month 2 | Month 3 | Month 4 | Month 5 |
| 1b | 118 | 150 | 399 | 420 | — |
| 2b | 100 | 250 | 420 | 460 | — |
| 3b | 04 | 93 | 190 | 320 | — |
| 4b | 667 | 550 | 815 | 830 | — |
| 5b | 160 | 120 | 480 | 620 | — |
| 6b | 210 | 190 | 520 | 510 | — |
| 7b | 420 | 500 | 780 | 780 | — |
| 8b | 128 | 108 | 310 | 304 | — |
| 9b | 110 | 150 | 380 | 348 | — |
| 10b | 380 | 460 | 716 | 716 | — |
| 11b | 300 | 410 | 390 | 560 | — |
| 12b | 100 | 120 | 310 | 318 | — |
| 13b | 250 | 180 | 340 | 420 | — |
| 14b | 80 | 70 | 260 | 380 | — |
| 15b | 140 | 110 | 300 | 420 | — |
| 16b | 250 | 180 | 290 | 360 | — |
| 17b | 300 | 380 | 460 | 580 | — |
| 18b | 280 | 290 | 290 | 410 | — |
| 19b | 118 | 190 | 170 | 320 | — |
| 20b | 160 | 160 | 220 | 299 | 360 |

Example 4

In another experiment, 21 HIV-positive subjects were treated with a herbal composition consisting of the 14 herbal ingredients identified in Table 2. Subjects were administered a composition prepared by dissolving approximately 1 tbsp. (or 15 ml) of the powdered ingredients (a mixture prepared the 14 plants listed in Table 2) in approximately 8 ozs. (250 ml) of hot water. The supernatant liquid was then ingested by the subject.

The subjects were divided into two groups: the first group having 10 subjects (subject ID Nos. 1-10) and the second group having 16 subjects (Subject ID Nos 11-26). In the first group, each of the 14 plants was present in the composition in equal weight ratios. In the second group, the concentrations of *Dovyalis abyssinica* and *Clutia robusta* were approximately half of the other 12 ingredients as disclosed.

As shown in Table 4, CD4 counts for each subject were measured on a monthly basis. The CD4 counts of the test subjects treated with the 14 ingredient herbal composition increased by up to 100 per month. Six subjects tested HIV-negative after four months of treatment. Two subjects tested HIV-negative after two months of treatment.

TABLE 4

CD4 Counts per Month

| Subject ID | $CD_{4/\mu L}$ per month | | | |
|---|---|---|---|---|
| | Month 1 | Month 2 | Month 3 | Month 4 |
| 1 | 420 | 450 | 570 | HIV negative |
| 2 | 320 | 390 | 480 | 520 |
| 3 | 100 | 115 | 250 | — |
| 4 | 80 | 150 | 310 | — |
| 5 | 340 | 370 | 480 | 560 |
| 6 | 120 | 180 | 299 | — |
| 7 | 118 | 350 | 360 | HIV negative |
| 8 | 125 | 105 | 225 | — |
| 9 | 300 | 200 | 400 | HIV negative |
| 10 | 280 | 399 | 410 | HIV negative |
| 11 | 400 | 500 | 520 | HIV negative |
| 12 | 250 | 250 | 310 | — |
| 13 | 250 | 460 | 600 | — |
| 14 | 400 | 520 | 780 | — |
| 15 | 250 | 330 | 480 | HIV negative |
| 16 | 667 | 550 | 815 | 830 |
| 17 | 150 | 250 | 380 | — |
| 18 | 620 | 640 | 660 | — |
| 19 | 310 | 400 | 480 | — |
| 20 | 243 | 245 | 280 | — |
| 21 | 180 | 216 | 434 | — |
| 22 | 280 | 390 | — | — |
| 23 | 360 | 420 | — | — |
| 24 | 190 | 280 | — | — |
| 25 | 630 | 720; HIV negative | — | — |
| 26 | N/A; HIV positive | N/A; HIV negative | — | — |

By comparison with the results achieved with the compositions having the disclosed compounds, in a study conducted on subjects on HAART in Moi University Teaching and Academic Model for Prevention and Treatment of HIV (AMPATH), the CD4 count increases were gradual, generally taking several years to reach above 500. The subjects were treated with conventional antiretroviral (ARV) therapy, consisting of twice daily dosing of Stavudine, Lamivudine and Nevirapine (d4T-3TC-NVP). Other ARV regimes include treatment with combinations consisting of ZDV-3TC-NVP, d4T-3TC-EFV and ZDV-3TC-EFV (wherein ZDV is Zidovudine and EFV is Efavirenz). Treatment guidelines are provided in the publication "Integrated Management of Adolescent and Adult Illness," published in January 2004 by the World Health Organization. ARV therapy subjects rarely reverse their seroconversion status, and among those listed in Table 5, none did so.

TABLE 5

Comparative Results of CD4 Count Increases

Comparative Results of CD4 Count Increases in Subjects Under Conventional ARV Therapy.

| | 6 Months | 1 Year | 1 1/2 Years | 2 Years | 2 1/2 Years | 3 Years |
|---|---|---|---|---|---|---|
| 1. | 247 | 207 | 264 | 197 | 138 | 367 |
| 2. | 315 | 327 | 150 | 260 | — | — |
| 3. | 268 | 199 | 195 | 360 | — | — |
| 4. | 99 | 163 | — | — | — | — |
| 5. | 265 | 40 | 36 | 247 | 332 | 397 |
| 6. | 138 | 311 | 584 | 578 | — | — |
| 7. | 37 | 298 | — | — | — | — |
| 8. | 201 | 261 | — | — | — | — |
| 9. | 21 | 52 | 74 | 309 | — | — |
| 10. | 2 | 156 | — | — | — | — |
| 11. | 43 | 200 | — | — | — | — |
| 12. | 169 | 295 | — | — | — | — |
| 13. | 75 | 144 | 179 | — | — | — |

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The plant parts described in the specification are those in which in the experience of the inventors, the highest concentration of beneficial ingredients are to be found. However, it will be apparent to those skilled in the art that the same or other beneficial compounds may be found in other parts of the recited plants not specifically disclosed herein, and that therefore, any composition comprised of any part or parts of the recited plants which includes *Dovyalis abyssinica* and *Clutia robusta* is within the scope of the invention.

While some detailed embodiments have been illustrated and described, it should be understood that such detailed embodiments are merely exemplary and changes and modifications can be made therein in accordance with ordinary skill in the art without departing from the invention in its broader aspects as defined in the following claims.

What is claimed is:

1. A composition comprising:
   (a) at least one of the following isolated compounds:
      N-Methyl-L-tryptophan;
      1,2-Methylenedioxy-9-hydroxy-10-methoxynoraporphine;
      6-(1,2,3,4-Tetrahydro-6,7-dimethoxy-2-methyl-1-isoquinolinyl)furo[3,4-e]-1,3-benzodioxol-8(6H)-one; or
      [1,α,3β(E),5α,6α,7α]-2-Methyl-2-butenoic acid-6,7-dihydroxy-8-methyl-8-azabicyclo[3.2.1]oct-3-yl ester, and
   (b) at least one of the following isolated compounds:
      (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
      3β-(Hydroxymethyl)-2α-methyl-4β-[(9-methyl-9H-pyrido[3,4-b]indol-1-yl)methyl]-2H-pyran-5-carboxylic acid methyl ester; or
      (3aS-cis)-1,2,3,3a,8,8a-Hexahydro-1,3a,8-trimethylpyrrolo[2,3-b]indol-5-ol methylcarbamate (ester).

2. The composition of claim 1 comprising the following isolated compounds:
   N-Methyl-L-tryptophan;
   1,2-Methylenedioxy-9-hydroxy-10-methoxynoraporphine;
   6-(1,2,3,4-Tetrahydro-6,7-dimethoxy-2-methyl-1-isoquinolinyl)furo[3,4-e]-1,3-benzodioxol-8(6H)-one;
   [1,α,3β(E),5α,6α,7α]-2-Methyl-2-butenoic acid-6,7-dihydroxy-8-methyl-8-azabicyclo[3.2.1]oct-3-yl ester;
   (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
   3β-(Hydroxymethyl)-2α-methyl-4β-[(9-methyl-9H-pyrido[3,4-b]indol-1-yl)methyl]-2H-pyran-5-carboxylic acid methyl ester; and
   (3aS-cis)-1,2,3,3a,8,8a-Hexahydro-1,3a,8-trimethylpyrrolo[2,3-b]indol-5-ol methylcarbamate(ester).

3. The composition of claim 1, further comprising at least one of the following isolated compounds:
   (1α,2β)-3,12-Dihehydro-9,10-[methylenebis(oxy)]galanthan-1,2-diol;
   (3β,12α)-Solanid-5-ene-3,12-diol;
   1-(6-methoxy-4-quinolyl)-3-(3-vinyl-4-piperidyl)-1-propanone;
   (E,E,Z)-N-isobutyl-2,6,8-decatrienamide; 2,3,5,6-tetramethoxyphenanthro[9,10:6',7']indolizidine;
   5,7,8,15-Tetrahydro-3,4-dimethoxy-6-methylbenzo[e][1,3]dioxolo[4,5-k][3]benzazecin-14(6H)-one;
   (1S,6S,7R,8R,8aR)-Octahydro-indolizinetetrol;
   (3S,4R)-Dihydro-3-[(R)-hydroxyphenylmethyl]-4-[(1-methyl-1H-imidazol-5-yl)methyl]-2(3H)-furanone;
   (3S-cis)-3-Ethyldihdroxy-4-[(-methyl-1H-imidazol-5-yl)methyl]-2(3H)-furanone;
   (S)-4-Ethyl-4-hydroxy-1H-pyrano[3'4':6,7]indolizino[1,2-b]quinoline-3,14(4H,12H)-dione;
   1,2,3,4-Tetrahydro-6,7-dimethoxy-8-isoquinolinol;
   1,2,3,4-Tetrahydro-6,7-dimethoxy-1-methyl-8-isoquinolinol;
   N-(7S)-5,6,7,9-Tetrahydro-1,2,3,10-tetramethoxy-9-oxobenzo[a]heptalen-7-yl]acetamide;
   1αH,5αH-tropan-3α-ol atropate;
   1,2-(methylenedioxy)-6aβ-aporphin-11-ol;
   (16α,17α)-17-Hydroxyyohimban-16-carboxylic acid methyl ester;
   trans-8-methyl-N-vanillyl-6-nonenamide;
   1,2-(methylenedioxy)aporphine;
   (1R-trans)-2,3,5,7a-Tetrahydro-1-hydroxy-1H-pyrrolizine-7-methanol;
   [1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;
   (3α,14β,16α)-14,15-Dihydro-14-hydroxyeburnamenine-14-carboxylic acid methyl ester;
   1,10-Dimethoxy-6aα-aporhine-2,9-diol;
   6,7,12b,13-Tetrahydro-4H-bis[1,3]benzodioxolo[5,6-a:4',5'-g]quinolizine;
   (8β)-8-methoxy-16-methyl-2,3:10,11-bis[methylenebis(oxy)]rheadan;
   6',7',10,11-Tetramethoxyemetan;
   3-(-Benzoyloxy)-8-methyl-8-azabicyclo[3.2.1]octane-2-carboxylic acid;
   8,13,13b,14-Tetrahydro-14-methylindolo[2',3':3,4]pyrido[2,1-b]quinazolin-5(7H)-one;
   6',12'-Dimethoxy-2,2'-dimethyl-6,7-[methylenebis(oxy)]oxyacanthan;
   4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;
   5,11-Dimethyl-6H-pyrido[4,-3b]carbazole;
   6,7-Dihydro-1,2,3,10-tetramethoxy-7-(methylamino)benzo[a]heptalen-9(5H)-one;
   (1α)-2,3-Didehydro-7-methoxycrinan-1-ol; or
   (1α,3α)-7-methoxycrinan-1,3-diol.

4. The composition of claim 1 comprising the following isolated compounds:
   N-Methyl-L-tryptophan;
   1,2-Methylenedioxy-9-hydroxy-10-methoxynoraporphine;
   6-(1,2,3,4-Tetrahydro-6,7-dimethoxy-2-methyl-1-isoquinolinyl)furo[3,4-e]-1,3-benzodioxol-8(6H)-one;
   [1,α,3β(E),5α,6α,7α]-2-Methyl-2-butenoic acid-6,7-dihydroxy-8-methyl-8-azabicyclo[3.2.1]oct-3-yl ester;
   (6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
   3β-(Hydroxymethyl)-2α-methyl-4β-[(9-methyl-9H-pyrido[3,4-b]indol-1-yl)methyl]-2H-pyran-5-carboxylic acid methyl ester;
   (3aS-cis)-1,2,3,3a,8,8a-Hexahydro-1,3a,8-trimethylpyrrolo[2,3-b]indol-5-ol methylcarbamate (ester);
   (1α,2β)-3,12-Dihehydro-9,10-[methylenebis(oxy)]galanthan-1,2-diol;
   (3β,12α)-Solanid-5-ene-3,12-diol;
   1-(6-methoxy-4-quinolyl)-3-(3-vinyl-4-piperidyl)-1-propanone;
   (E,E,Z)-N-isobutyl-2,6,8-decatrienamide;
   2,3,5,6-tetramethoxyphenanthro[9,10:6',7']indolizidine;

5,7,8,15-Tetrahydro-3,4-dimethoxy-6-methylbenzo[e][1,3]dioxolo-[4,5-k][3]benzazecin-14(6H)-one;
(1S,6S,7R,8R,8aR)-Octahydro-indolizinetetrol;
(3S,4R)-Dihydro-3-[(R)-hydroxyphenylmethyl]-4-[(1-methyl-1H-imidazol-5-yl)methyl]-2(3H)-furanone;
(3S-cis)-3-Ethyldihdroxy-4-[(-methyl-1H-imidazol-5-yl)methyl]-2(3H)-furanone;
(S)-4-Ethyl-4-hydroxy-1H-pyrano[3'4':6,7]indolizino[1,2-b]quinoline-3,14(4H,12H)-dione;
1,2,3,4-Tetrahydro-6,7-dimethoxy-8-isoquinolinol;
1,2,3,4-Tetrahydro-6,7-dimethoxy-1-methyl-8-isoquinolinol;
N-(7S)-5,6,7,9-Tetrahydro-1,2,3,10-tetramethoxy-9-oxobenzo[a]heptalen-7-yl]acetamide;
1αH,5αH-tropan-3α-ol atropate;
1,2-(methylenedioxy)-6aβ-aporphin-11-ol;
(16α,17α)-17-Hydroxyyohimban-16-carboxylic acid methyl ester;
trans-8-methyl-N-vanillyl-6-nonenamide;
1,2-(methylenedioxy)aporphine;
(1R-trans)-2,3,5,7a-Tetrahydro-1-hydroxy-1H-pyrrolizine-7-methanol;
[1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;
(3α,14β,16α)-14,15-Dihydro-14-hydroxyeburnamenine-14-carboxylic acid methyl ester;
1,10-Dimethoxy-6aα-aporhine-2,9-diol;
6,7,12b,13-Tetrahydro-4H-bis[1,3]benzodioxolo[5,6-a:4',5'-g]quinolizine;
(8β)-8-methoxy-16-methyl-2,3:10,11-bis[methylenebis(oxy)]rheadan;
6',7',10,11-Tetramethoxyemetan;
3-(-Benzoyloxy)-8-methyl-8-azabicyclo[3.2.1]octane-2-carboxylic acid;
8,13,13b,14-Tetrahydro-14-methylindolo[2',3':3,4]pyrido[2,1-b]quinazolin-5(7H)-one;
6',12'-Dimethoxy-2,2'-dimethyl-6,7-[methylenebis(oxy)]oxyacanthan;
4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;
5,11-Dimethyl-6H-pyrido[4,-3b]carbazole;
6,7-Dihydro-1,2,3,10-tetramethoxy-7-(methylamino)benzo[a]heptalen-9(5H)-one;
(1α)-2,3-Didehydro-7-methoxycrinan-1-ol; and
(1α,3α)-7-methoxycrinan-1,3-diol.

5. The composition of claim 1, comprising:
(a) at least one of the following isolated compounds:
N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one; or
[1,α,3β(E),5α,6α,7α]-2-Methyl-2-butenoic acid-6,7-dihydroxy-8-methyl-8-azabicyclo[3.2.1]oct-3-yl ester,
(b) at least one of the following isolated compounds:
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; or
(3aS-cis)-1,2,3,3a,8,8a-Hexahydro-1,3a,8-trimethylpyrrolo[2,3-b]indol-5-ol methylcarbamate(ester), and
(c) a carrier.

6. A composition consisting essentially of a carrier and at least two alkaloid compounds, wherein the at least two alkaloid compounds are:
(a) at least one of:
N-Methyl-L-tryptophan;
1,2-Methylenedioxy-9-hydroxy-10-methoxynoraporphine;
6-(1,2,3,4-Tetrahydro-6,7-dimethoxy-2-methyl -1-isoquinolinyl)furo[3,4-e]-1,3-benzodioxol-8(6H)-one; or
[1,α,3β(E),5α,6α,7α]-2-Methyl-2-butenoic acid-6,7-dihydroxy-8-methyl-8-azabicyclo[3.2.1]oct-3-yl ester, and
(b) at least one of:
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; or
(3aS-cis)-1,2,3,3a,8,8a-Hexahydro-1,3a,8-trimethylpyrrolo[2,3-b]indol-5-ol methylcarbamate(ester).

7. The composition of claim 6 consisting essentially of a carrier and at least the following alkaloid compounds:
N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)-one;
[1,α,3β(E),5α,6α,7α]-2-Methyl-2-butenoic acid-6,7-dihydroxy-8-methyl-8-azabicyclo[3.2.1]oct-3-yl ester;
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; and
(3aS-cis)-1,2,3,3a,8,8a-Hexahydro-1,3a,8-trimethylpyrrolo[2,3-b]indol-5-ol methylcarbamate(ester).

8. A composition consisting essentially of a carrier and at least two alkaloid compounds, wherein the at least two alkaloid compounds are:
(a) at least one of:
N-Methyl-L-tryptophan;
1,2-Methylenedioxy-9-hydroxy-10-methoxynoraporphine;
6-(1,2,3,4-Tetrahydro-6,7-dimethoxy-2-methyl-1-isoquinolinyl)furo[3,4-e]-1,3-benzodioxol-8(6H)one; or
[1,α,3β(E),5α,6α,7α]-2-Methyl-2-butenoic acid-6,7-dihydroxy-8-methyl-8-azabicyclo[3.2.1]oct-3-yl ester, and
(b) at least one of:
(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;
3β-(Hydroxymethyl)-2α-methyl-4β-[(9-methyl-9H-pyrido[3,4-b]indol-1-yl)methyl]-2H-pyran-5-carboxylic acid methyl ester; or (3aS-cis)-1,2,3,3a,8,8a-Hexahydro-1,3a,8-trimethylpyrrolo[2,3-b]indol-5-ol methylcarbamate(ester), and at least one of the following alkaloid compounds:

(1α,2β)-3,12-Dihehydro-9,10-[methylenebis(oxy)]galanthan-1,2-diol;

(3β,12α)-Solanid-5-ene-3,12-diol;

1-(6-methoxy-4-quinolyl)-3-(3-vinyl-4-piperidyl)-1-propanone;

(E,E,Z)-N-isobutyl-2,6,8-decatrienamide; 2,3,5,6-tetramethoxyphenanthro[9,10:6',7']indolizidine;

5,7,8,15-Tetrahydro-3,4-dimethoxy-6-methylbenzo[e][1,3]dioxolo[4,5-k][3]benzazecin-14(6H)-one;

(1S,6S,7R,8R,8aR)-Octahydro-indolizinetetrol;

(3S,4R)-Dihydro-3-[(R)-hydroxyphenylmethyl]-4-[(1-methyl-1H-imidazol-5-yl)methyl]-2(3H)-furanone;

(3S-cis)-3-Ethyldihydroxy-4-[(-methyl-1H-imidazol-5-yl)methyl]-2(3H)-furanone;

(S)-4-Ethyl-4-hydroxy-1H-pyrano[3'4':6,7]indolizino[1,2-b]quinoline-3,14(4H,12H)-dione;

1,2,3,4-Tetrahydro-6,7-dimethoxy-8-isoquinolinol;

1,2,3,4-Tetrahydro-6,7-dimethoxy-1-methyl-8-isoquinolinol;

N-(7S)-5,6,7,9-Tetrahydro-1,2,3,10-tetramethoxy-9-oxobenzo[a]heptalen-7-yl]acetamide;

1αH,5αH-tropan-3α-ol atropate;

1,2-(methylenedioxy)-6aβ-aporphin-11-ol;

(16α,17α)-17-Hydroxyyohimban-16-carboxylic acid methyl ester;

trans-8-methyl-N-vanillyl-6-nonenamide;

1,2-(methylenedioxy)aporphine;

(1R-trans)-2,3,5,7a-Tetrahydro-1-hydroxy-1H-pyrrolizine-7-methanol;

[1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;

(3α,14β,16α)-14,15-Dihydro-14-hydroxyeburnamenine-14-carboxylic acid methyl ester;

1,10-Dimethoxy-6aα-aporhine-2,9-diol;

6,7,12b,13-Tetrahydro-4H-bis[1,3]benzodioxolo[5,6-a:4',5'-g]quinolizine;

(8β)-8-methoxy-16-methyl-2,3:10,11-bis[methylenebis(oxy)]rheadan;

6',7',10,11-Tetramethoxyemetan;

3-(-Benzoyloxy)-8-methyl-8-azabicyclo[3.2.1]octane-2-carboxylic acid;

8,13,13b,14-Tetrahydro-14-methylindolo[2',3':3,4]pyrido[2,1-b]quinazolin-5(7H)-one;

6',12'-Dimethoxy-2,2'-dimethyl-6,7-[methylenebis(oxy)]oxyacanthan;

4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;

5,11-Dimethyl-6H-pyrido[4,-3b]carbazole;

6,7-Dihydro-1,2,3,10-tetramethoxy-7-(methylamino) benzo[a]heptalen-9(5H)-one;

(1α)-2,3-Didehydro-7-methoxycrinan-1-ol; or (1α,3α)-)-7-methoxycrinan-1,3-diol.

9. The composition of claim 6, consisting essentially of a carrier and the following alkaloid compounds:

N-Methyl-L-tryptophan;

1,2-Methylenedioxy-9-hydroxy-10-methoxynoraporphine;

6-(1,2,3,4-Tetrahydro-6,7-dimethoxy-2-methyl-1-isoquinolinyl)furo[3,4-e]-1,3-benzodioxol-8(6H)-one;

[1,α,3β(E),5α,6α,7α]-2-Methyl-2-butenoic acid-6,7-dihydroxy-8-methyl-8-azabicyclo[3.2.1]oct-3-yl ester;

(6aS)-9-[4,5-Dimethoxy-2-[[(1S)-1,2,3,4-tetrahydro-6,7-dimethoxy-2-methyl-1-isoquinolinyl]methyl]phenoxy]-5,6,6a,7-tetrahydro-1,2,10-trimethoxy-6-methyl-4H-dibenzo[de,g]quinoline;

3β-(Hydroxymethyl)-2α-methyl-4β-[(9-methyl-9H-pyrido[3,4-b]indol-1-yl)methyl]-2H-pyran-5-carboxylic acid methyl ester;

(3aS-cis)-1,2,3,3a,8,8a-Hexahydro-1,3a,8-trimethylpyrrolo[2,3-b]indol-5-ol methylcarbamate (ester);

(1α,2β)-3,12-Dihehydro-9,10-[methylenebis(oxy)]galanthan-1,2-diol;

(3β,12α)-Solanid-5-ene-3,12-diol;

1-(6-methoxy-4-quinolyl)-3-(3-vinyl-4-piperidyl)-1-propanone;

(E,E,Z)-N-isobutyl-2,6,8-decatrienamide;

2,3,5,6-tetramethoxyphenanthro[9,10:6',7']indolizidine;

5,7,8,15-Tetrahydro-3,4-dimethoxy-6-methylbenzo[e][1,3]dioxolo-[4,5-k][3]benzazecin-14(6H)-one;

(1S,6S,7R,8R,8aR)-Octahydro-indolizinetetrol;

(3S,4R)-Dihydro-3-[(R)-hydroxyphenylmethyl]-4-[(1-methyl-1H-imidazol-5-yl)methyl]-2(3H)-furanone;

(3S-cis)-3-Ethyldihdroxy-4-[(-methyl-1H-imidazol-5-yl)methyl]-2(3H)-furanone;

(S)-4-Ethyl-4-hydroxy-1H-pyrano(3'4':6,7]indolizino[1,2-b]quinoline-3,14(4H,12H)-dione;

1,2,3,4-Tetrahydro-6,7-dimethoxy-8-isoquinolinol;

1,2,3,4-Tetrahydro-6,7-dimethoxy-1-methyl-8-isoquinolinol;

N-(7S)-5,6,7,9-Tetrahydro-1,2,3,10-tetramethoxy-9-oxobenzo[a]heptalen-7-yl]acetamide;

1αH,5αH-tropan-3α-ol atropate;

1,2-(methylenedioxy)-6aβ-aporphin-11-ol;

(16α,17α)-17-Hydroxyyohimban-16-carboxylic acid methyl ester;

trans-8-methyl-N-vanillyl-6-nonenamide;

1,2-(methylenedioxy)aporphine;

(1R-trans)-2,3,5,7a-Tetrahydro-1-hydroxy-1H-pyrrolizine-7-methanol;

[1R-(1α,2E,4aα,4bβ,8aα,10aβ)]-(Dodecahydro-7-hydroxy-1,4b,8,8-tetramethyl-10-oxo-2(H)-phenanthrenylidene) acetic acid 2-(dimethylamino)ethyl ester;

(3α,14β,16α)-14,15-Dihydro-14-hydroxyeburnamenine-14-carboxylic acid methyl ester;

1,10-Dimethoxy-6aα-aporhine-2,9-diol;

6,7,12b,13-Tetrahydro-4H-bis[1,3]benzodioxolo[5,6-a:4',5'-g]quinolizine;

(8β)-8-methoxy-16-methyl-2,3:10,11-bis[methylenebis(oxy)]rheadan;

6',7',10,11-Tetramethoxyemetan;

3-(-Benzoyloxy)-8-methyl-8-azabicyclo[3.2.1]octane-2-carboxylic acid;

8,13,13b,14-Tetrahydro-14-methylindolo[2',3':3,4]pyrido[2,1-b]quinazolin-5(7H)-one;

6',12'-Dimethoxy-2,2'-dimethyl-6,7-[methylenebis(oxy)]oxyacanthan;

4-[[(1R)-1,2,3,4-Tetrahydro-6,7-dimethoxy-2-methyl-1-isoquinolinyl]methyl]-2-[4-[[(1R)-1,2,-3,4-tetrahydro-6,7-dimethoxy-2-methyl-1-isoquinolinyl]methyl]-phenoxylphenol;

5,11-Dimethyl-6H-pyrido[4,-3b]carbazole;

6,7-Dihydro-1,2,3,10-tetramethoxy-7-(methylamino) benzo[a]heptalen-9(5H)-one;

(1α)-2,3-Didehydro-7-methoxycrinan-1-ol; and (1α,3α)-7-methoxycrinan-1,3-diol.

10. The composition of claim 1, wherein the composition is in solid form.

11. The composition of claim 1, wherein the composition is substantially free of non-alkaloid plant material.

12. The composition of claim 1, wherein the composition is substantially free of plant material.

13. The composition of claim 1, wherein the composition is a pharmaceutical composition and the carrier is a pharmaceutically acceptable carrier.

* * * * *